United States Patent
Christiano

(10) Patent No.: US 11,957,678 B2
(45) Date of Patent: *Apr. 16, 2024

(54) METHODS FOR INDUCING AN IMMUNE RESPONSE

(71) Applicant: MOONSHOT PHARMA LLC, New York, NY (US)

(72) Inventor: Angela Christiano, Mahwah, NJ (US)

(73) Assignee: MOONSHOT PHARMA LLC, New York, NY (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/479,029

(22) Filed: Sep. 20, 2021

(65) Prior Publication Data

US 2022/0000865 A1    Jan. 6, 2022

Related U.S. Application Data

(63) Continuation of application No. 16/065,745, filed as application No. PCT/US2016/068591 on Dec. 23, 2016, now Pat. No. 11,135,221.

(60) Provisional application No. 62/387,565, filed on Dec. 23, 2015.

(51) Int. Cl.
| | |
|---|---|
| A61K 31/498 | (2006.01) |
| A61K 31/15 | (2006.01) |
| A61K 31/4245 | (2006.01) |
| A61K 31/427 | (2006.01) |
| A61K 31/4439 | (2006.01) |
| A61K 31/496 | (2006.01) |
| A61K 39/395 | (2006.01) |
| A61K 45/06 | (2006.01) |
| A61P 35/00 | (2006.01) |
| C07K 16/28 | (2006.01) |
| A61K 39/00 | (2006.01) |

(52) U.S. Cl.
CPC ............ *A61K 31/498* (2013.01); *A61K 31/15* (2013.01); *A61K 31/4245* (2013.01); *A61K 31/427* (2013.01); *A61K 31/4439* (2013.01); *A61K 31/496* (2013.01); *A61K 39/3955* (2013.01); *A61K 45/06* (2013.01); *A61P 35/00* (2018.01); *C07K 16/2818* (2013.01); *A61K 2039/505* (2013.01); *A61K 2039/507* (2013.01); *A61K 2039/53* (2013.01)

(58) Field of Classification Search
CPC ................................................... A61K 31/498
See application file for complete search history.

(56) References Cited

U.S. PATENT DOCUMENTS

| | | |
|---|---|---|
| 4,708,871 A | 11/1987 | Geysen |
| 4,833,092 A | 5/1989 | Geysen |
| 5,223,409 A | 6/1993 | Ladner et al. |
| 5,403,484 A | 4/1995 | Ladner et al. |
| 5,427,908 A | 6/1995 | Dower et al. |
| 5,432,108 A | 7/1995 | Lee |
| 5,498,530 A | 3/1996 | Schatz et al. |
| 5,556,762 A | 9/1996 | Pinilla et al. |
| 5,571,689 A | 11/1996 | Heuckeroth et al. |
| 5,580,717 A | 12/1996 | Dower et al. |
| 5,624,821 A | 4/1997 | Winter et al. |
| 5,648,260 A | 7/1997 | Winter et al. |
| 5,663,143 A | 9/1997 | Ley et al. |
| 5,698,426 A | 12/1997 | Huse |
| 5,723,286 A | 3/1998 | Dower et al. |
| 5,723,323 A | 3/1998 | Kauffman et al. |
| 5,734,018 A | 3/1998 | Rutter et al. |
| 5,750,373 A | 5/1998 | Garrard et al. |
| 5,763,192 A | 6/1998 | Kauffman et al. |
| 5,770,434 A | 6/1998 | Huse |
| 6,992,096 B2 | 1/2006 | Karp et al. |
| 8,163,782 B2 | 4/2012 | Karp et al. |
| 8,227,494 B2 | 7/2012 | Karp et al. |
| 8,716,321 B2 | 5/2014 | Hirawat et al. |
| 8,796,322 B2 | 8/2014 | Karp et al. |
| 10,996,976 B2 | 3/2021 | Christiano |
| 11,135,221 B2 * | 10/2021 | Christiano ......... A61K 39/3955 |
| 2004/0214193 A1 | 10/2004 | Eisenlohr et al. |
| 2006/0166926 A1 | 7/2006 | Wilde et al. |
| 2006/0167263 A1 | 7/2006 | Wilde et al. |
| 2007/0135473 A1 | 6/2007 | Semov et al. |
| 2007/0203123 A1 | 8/2007 | Wilde et al. |
| 2008/0207538 A1 | 8/2008 | Lawrence et al. |

(Continued)

FOREIGN PATENT DOCUMENTS

| | | |
|---|---|---|
| WO | 1984003506 A1 | 9/1984 |
| WO | 1984003564 A1 | 9/1984 |

(Continued)

OTHER PUBLICATIONS

Lewis et al. "Evidence for the Widespread Coupling of Alternative Splicing and Nonsense-Mediated mRNA Decay in Humans" Jan. 7, 2003, PNAS USA 100(1): 189-192.
Li et al. "Nonsense Surveillance in Lymphocytes?" Feb. 1998, Immunity 8:135-141.
Linde et al. "Introducing Sense into Nonsense in Treatments of Human Genetic Diseases" Nov. 1, 2008, Trends in Genetics 24(11):552-563.
Loudon "Ataluren: a 'no nonsense' Approach for Pulmonary Diseases" Jun. 2013,Pulmonary Pharmacol. Therap. 26(3):398-399.
Loufrani et al. "Absence of Dystrophin in Mice Reduces NO-dependent Vascular Funcction and Vascular Density: Total Recovery After a Treatment with the Aminoglycoside Gentamicin" Apr. 2004, Arterioscler. Thromb. Vasc. Biol. 24(4):671-676.

(Continued)

*Primary Examiner* — Rei Tsang Shiao
(74) *Attorney, Agent, or Firm* — Troutman Pepper Hamilton Sanders LLP (Rochester)

(57) ABSTRACT

Provided herein, inter alia, are compositions and methods for generating a immune response in an individual and/or inducing the expression of neoantigens on the surface of abnormal (such as proliferative) cells via promotion of premature termination codon (PTC) read-through and inhibition of nonsense-mediated decay (NMD) of messenger RNAs (mRNAs) bearing PTCs.

20 Claims, 3 Drawing Sheets

(56) References Cited

U.S. PATENT DOCUMENTS

| | | |
|---|---|---|
| 2009/0032592 A1 | 2/2009 | Christensen |
| 2009/0149513 A1 | 6/2009 | Hirawat et al. |
| 2009/0203752 A1 | 8/2009 | Campbell et al. |
| 2010/0093867 A1 | 4/2010 | Matsuda et al. |
| 2011/0003843 A1 | 1/2011 | Lejeune et al. |
| 2011/0046136 A1 | 2/2011 | Almstead et al. |
| 2012/0087896 A1 | 4/2012 | Almstead et al. |
| 2012/0263740 A1 | 10/2012 | Gilboa et al. |
| 2013/0217717 A1 | 8/2013 | Lejeune et al. |
| 2013/0224237 A1 | 8/2013 | Gilboa |
| 2013/0289007 A1 | 10/2013 | Karp et al. |
| 2013/0293637 A1 | 11/2013 | Bacon et al. |
| 2014/0094457 A1 | 4/2014 | Gardner et al. |
| 2015/0051251 A1 | 2/2015 | Gatti et al. |
| 2015/0202223 A1 | 7/2015 | Lee et al. |
| 2015/0274674 A1 | 10/2015 | Almstead et al. |
| 2015/0290207 A1 | 10/2015 | Kutok et al. |
| 2016/0015709 A1 | 1/2016 | Cheresh et al. |
| 2017/0226221 A1 | 8/2017 | Madiyalakan et al. |

FOREIGN PATENT DOCUMENTS

| | | |
|---|---|---|
| WO | 1994029351 A2 | 12/1994 |
| WO | 1997015390 A1 | 5/1997 |
| WO | 1999051642 A1 | 10/1999 |
| WO | 2000000823 A1 | 1/2000 |
| WO | 2000039585 A1 | 7/2000 |
| WO | 2001044516 A2 | 6/2001 |
| WO | 2004009533 A1 | 1/2004 |
| WO | 2004009558 A2 | 1/2004 |
| WO | 2004009610 A2 | 1/2004 |
| WO | 2008101935 A2 | 8/2008 |
| WO | 2011005566 A2 | 1/2011 |
| WO | 2012016930 A1 | 2/2012 |
| WO | 2013142346 A1 | 9/2013 |
| WO | 2014055644 A2 | 4/2014 |
| WO | 2015035091 A1 | 3/2015 |
| WO | 2015109248 A1 | 7/2015 |
| WO | 2015134711 A1 | 9/2015 |
| WO | 2015143441 A1 | 9/2015 |
| WO | 2017015442 A1 | 1/2017 |
| WO | 2017102954 A1 | 6/2017 |
| WO | 2017102955 A1 | 6/2017 |
| WO | 2017102956 A1 | 6/2017 |
| WO | 2018237326 A1 | 12/2018 |

OTHER PUBLICATIONS

Makrides "Gene Transfer and Expression in Mamalian Cells" 2003 Ed., Elsvier Sciences B.V., Amsterdam (Title Page and TOC only).

Martin et al. "Identification and Characterization of Small Molecules that Inhibit Nonsense-Mediated RNA Decay and Suppress Nonsense p53 Mutations" Jun. 1, 2014, Cancer Research 74(11):3104-3113.

Martin et al. "The Microtubule-depolymerizing Agent Ansamitocin P3 Programs Dendritic Cells Toward Enhanced Anti-tumor Immunity" Jun. 7, 2014, Cancer Immunology, Immunotherapy, NIH Author Manuscript 63(9):925-938.

McKinney et al. "Structural Insights Lead to a Negamycin Analogue with Improved Antimicrobial Activity Against Gram-Negative Pathogens" Jul. 12, 2015, ACS Med. Chem. Let. 6:930-955.

Mullis et al. "PCR: The Polymerase Chain Reaction" 1994 Ed. Birkhauser (Title Page and TOC only).

Needels et al. "Generation and Screening of an Oligonucleotide-Encoded Synthetic Peptide Library" Nov. 15, 1993 PNAS USA 90(22):10700-10704.

Nguyen et al. "Nonsense-mediated mRNA Decay: Inter-individual Variability and Human Disease" Oct. 1, 2014, Neuroscience and Biobehavioral Reviews 46:175-186.

Piekarz et al. "Epigenetic Modifiers: Basic Understanding and Clinical Development" Jun. 2009, Clinical Cancer Research 15(12):3918-3926.

Pilotte et al. "Reversal of Tumoral Immune Resistance bby Inhibition of Tryptophan 2,3-Dioxygenase" Feb. 14, 2012, PNAS USA 109(7):2497-2502.

Politano et al. "Gentamicin Administration in Duchenne Patients with Premature Stop Codon. Preliminary Results" 2003, Acta Myol. 22:15-21.

Popp et al. "Attenuation of Nonsense-mediated mRNA Decay Facilitates the Response to Chemotherapeutics" Mar. 26, 2015, Nature Communications 6(1) abstract.

Rebibo-Sabbah et al. "In Vitro and Ex Vivo Suppression by Aminoglycosides of PCDH15 Nonsense Mutations and Underlying Type 1 Usher Syndrome" Jul. 25, 2007, Hum. Genet. 122:373-381.

Sambrook et al. "Molecular Cloning: A Laboratory Manual" 2001, 3rd Ed. Cold Spring Harbor Press, Cold Spring Harbor, NY (Title Page and TOC only).

Sambrook et al. "Molecular Cloning: A Laboratory Manual" Fourth Ed, 2012 (TOC and Contents only).

Sausville et al. "Contribution sof Human Tumor Xenografts to Anticancer Drug Development" Apr. 1, 2006, Cancer Research 66(7):3351-3354.

Smith "Vaccinia Virus Vectors for Gene Expression" 1991, Current Opin. Biotechnol. 2:713-717.

Smith et al. "Correction: IDO is a Nodal Pathogenic Drive of Lung Cancer and Metastasis Development" Nov. 26, 2012, Cancer Discov. 2(8):722-735.

Sossi et al. "Premature Termination Mutations in exon 3 of the SMN1 Gene are Associated with Exon Skipping and a Relatively Mild SMA Phenotype" 2001, Eur. J. Hum. Genet. 9:113-120.

Supplementary European Search Report and Written Opinion for EP 16880163 mailed Sep. 30, 2019.

Supplementary European Search Report and Written Opinion for EP 16880164 mailed Oct. 1, 2019.

Supplementary European Search Report and Written Opinion for EP 16880165 mailed Sep. 30, 2019.

Tomoka et al. "Rigosertib Induces Cell Death of a Myelodysplastic Syndrome-derived Cell Line by DNA Damage-induced G2/M Arrest" Mar. 2015, Cancer Science 106(3):287-293.

Usuki et al. "Inhibition of SMG-8, a Subunit of SMG-1 Kinase, Ameliorates Nonsense-mediated mRNA Decay-exacerbated Mutant Phenotypes Without Cytotoxicity" Aug. 27, 2013, PNAS 110(37):15037-15042.

Weinmann "Cancer Immunotherapy: Selected Targets and Small-Molecule Modulators" Feb. 2, 2016, ChemMedChem. 11(5):450-466.

Xiao-Dong et al. "Pivotal Roles of cGAS-cGAMP Signaling in Antiviral Defense and Immune Adjuvant Effects" Sep. 20, 2013, Science 341(6152)a;1390-1394.

Zhan et al. "From Monoclonal Antibodies to Small Molecules: The Development of Inhibitors Targeting the PD-1/PD-L1 Pathway" Jun. 2016, Drug Disc. Today 21(6):1027-1036.

Zilberberg et al. "Restoration of APC Gene Function in Colorectal Cancer Cells by Aminoglycoside- and Macroline- induced Reatthrough of Premature Termination Codons" Dec. 1, 2009, GUT 59(4):496-507.

Adams et al. "Big Opportunities for Small Molecules in Immuno-Oncology" Sep. 2015, Nature Rev. Drug. Disc. 14:603-622.

Ausubel et al. "Current Protocols in Molecular Biology" 1987 Ed. John Wiley & Sons, Inc., New York, NY (Title Page and TOC only).

Beaucage et al. Current Protocols in Nucleic Acid Chemistry, 2000 Ed. John Wiley & Sons, Inc., New York, NY (Title Page and TOC only).

Behm-Ansmant et al. "Quality Control of Gene Expression: a Stepwise Assembly Pathway for the Surveillance Complex that Triggers Nonsense-mediated mRNA Decay" Feb. 15, 2006, Genes & Development 20(4):391-398.

Bidou et al. "Sense from Nonsense: Therapies for Premature Stop Codon Diseases" Nov. 1, 2012, Molecular Medicine Today 18(11):679-688.

Bordeira-Carrico et al. "Cancer Syndromes and Therapy by Stop-Codon Readthrough" Nov. 2012, Trends in Molecular Medicine 18(11):667-678.

(56) References Cited

OTHER PUBLICATIONS

Buck et al. "Stop Codon Read-through of a Methylamalonic Aciduria Mutation" Aug. 1, 2009, Molecular Genetics and Metabolism Academic Press 97(4):244-249.
Chakradhar et al. "Bringing RNA Into the Fold: Small Molecules Find New Targets in RNA to Combat Disease" May 2017, Nature Medicine 23(5):532-534.
Clackson et al. "Making Antibody Fragments Using Phase Display Libraries" Aug. 15, 1991, Nature 352:624-628.
Culbertson "RNA Surveillance: Unforeseen Consequences for Gene Expression, Inherited Genetic Disorders and Cancer" Feb. 1, 1999, Trends in Genetics 15(2):74-80.
Curran et al. "PD-1 and CTLA-4 Combination Blockade Expands Infiltrating T Cells and Reduces Regulatory T and Myeloid Cells Within B16 Melanoma Tumors" Mar. 2, 2010, PNAS USA 107(9):4275-4280.
Derosa et al. "Alternative Splicing and Nonsense-mediated mRNA Decay in the Regulation of a New Adenomatous Polyposis Coli Transcript" May 5, 2007, Gene 395(1-2):8-14.
Diner et al. "The Innate Immune DNA Sensor cGAS Produces a Noncanonical Cyclic Dinucleotide that Activates Human STING" May 30, 2013, Cell Rep. 3(5):1355-1361.
Du et al. "A New Series of Small Molecular Weight Compounds Induce Read Through of All Three Types of Nonsense Mutations in the ATM Gene" Sep. 1, 2013, Molecular Therapy 21(9):1653-1660.
Du et al. "Aminoglycoside Suppression of a Premature Stop Mutation in a Cftr-/-mouse Carrying a human CFTR-G542X Transgene" Jul. 3, 2002, J. Mol. Med. 80:595-604.
Du et al. "Nonaminoglycoside Compounds Induce Readthrough of Nonsense Mutations" Sep. 21, 2009, J. Exp. Med. 206(10):2285-2297.
Duncan et al. "The Binding Site for C1q on IgG" Apr. 21, 1988, Nature 332:738-740.
Duraiswamy et al. "Dual Blockade of PD-1 and CTLA-4 Combined with Tumor Vaccine Effectively Restores T-Cell Rejection Function in Tumors" 2013, Cancer Research 73(12):3591-3603.
Duraiswamy et al. "Therapeutic PD-1 Pathway Blockade Augments with Other Modalities of Immunotherapy 5"Cell Function to Prevent Immune Decline in Ovarian Cancer" Dec. 1, 2013, Cancer Research 73(23):6900-6912.
Durand et al. "Inihibition of Nonsense-mediated mRNA Decay (NMD) by a New Chemical Molecule Reveals the Dynamic of NMD Factors in P-bodies" Sep. 24, 2007 J. Cell Biology 178(7):1145-1160.
Fernando et al. "Induction of Tumour Immunity by Targeted Inhibition of Nonsense-mediated mRNA Decay" May 13, 2010, Nature 465(7295):227-230.
Floquet et al. "Readthrough of Premature Termination Codons in the Adenomatous Polyposis Coli Gene Restores Its Biological Activity in Human Cancer Cells" Aug. 31, 2011, Plos One 6(8):e24125.
Floquet et al. "Rescue of Non-sense Mutated p53 Tumor Suppressor Gene by Aminoglycosides" Apr. 1, 2011, Nucleic Acids Research 39(8):3350-3362.
Geysen et al. "Small Peptides Induce Antibodies with a Sequence and Structural Requirement for Binding Antigen Comparable to Antibodies Raised Against the Native Protein" Jan. 1, 1985, PNAS USA 82(1):178-182.
Geysen et al. "Strategies for Epitope Analysis Using Peptide Synthesis" Sep. 24, 1987, J. Immunol. Meth. 102(2):259-274.
Geysen et al. "Use of Peptide Synthesis to Probe Viral Antigens for Epitopes to a Resolution of a Single Amino Acid" Jul. 1, 1984, PNAS USA 81(13):3998-4002.
Gilboa et al. "Reducing Toxicity of Immune Therapy Using Aptamer-Targeted Drug Delivery" 2105, Cancer Immunol. Res. 3(11);1195-1200.
Gray et al. "Combination of HDAC and Topoisomerase Inhibitors in Small Cell Lung Cancer" Jun. 2012, Cancer Biology & Therapy 13(8):614-622.
Greenfield "Antibodies: A Laboratory Manual" 2014, 2nd Ed., Cold Spring Harbor Press, Cold Spring Harbor, NY (Title Page and TOC only).
Harvey et al., Lippinocott's Illustrated Reviews: Pharmacology, 2nd edition, 1997, Chapter 38, p. 373.
Helip-Wooley et al. "Expression of CTNS Alleles: Subcellular Localization and Aminoglycoside Correction in Vitro" Feb. 2002, Mol. Genet. Metab. 75(2):128-133.
Hentze et al. "A Perfect Message: RNA Surveillance and Nonsense-Mediated Decay" Feb. 5, 1999, Cell 96:307-310.
Hirawat et al. "Safety, Tolerability, and Pharmacokinetics of PTC124, a Nonaminoglycoside Nonsense Mutation Suppressor, Following Single- and Multiple-Dose Administration to Healthy Male and Female Adult Volunteers" 2007, J. Cliin. Pharmacol. 47:430-444.
Holtmeier et al. "γδ T Cells Link Innate and Adaptive Immune Responses" 2005, Chemical Immunology and Allergy 86:151-183.
Horgan et al. "Current Protocols in Immunology" 1994, John Wiley & Sons, Inc., New York, NY (Title Page and TOC only).
Ino et al. "Role of the Immune Tolerance-Inducing Molecule Indoleamine 2,3-Dioxygenase in Gynecological Cancers" 2012, J. Cancer Sci. Ther. S13:001.
International Search Report and Written Opinion for PCT/US2016/068588 dated Mar. 31, 2017.
International Search Report and Written Opinion for PCT/US2016/068589 dated Mar. 31, 2017.
International Search Report and Written Opinion for PCT/US2016/068591 dated Mar. 29, 2017.
International Search Report and Written Opinion for PCT/US2018/039102 dated Sep. 27, 2018.
Ishikawa et al. "STING Regulates Intracellular DNA-Mediated, Type I Interferon-Dependent Innate Immunity" Oct. 8, 2009, Nature 461:788-792.
Jamila et al. "Nonsense-mediated mRNA Decay Impacts MSI-driven Carcinogenesis and Anti-Tumor Immunity in Colorectal Cancers" Jul. 9, 2008, Plos One 3(7):e2583.
Johnson et al. "Relationships between Drug Activity in NCI Preclinical in vitro and in vivo Models and early Clinical Trials" 2001, Br. J. Cancer 84(10):1424-1431.
Kang et al. "Evidence for Non-V3-Specific Neutralizing Antibodies that Interfere with gp120/CD4 Binding in Human Immunodeficiency Virus 1-infected Humans" Jul. 15, 1991, PNAS USA 88(14):6171-6175.
Kayali et al. "Read-Through Compound 13 Restores Dystrophin Expression and Improves Muscle Function in the mdx Mouse Model for Duchenne Muscular Dystrophy" Sep. 15, 2012, Hum. Mol. Gen. 21(18):4007-4020.
Keeling et al. "Clinically relevant aminoglycosides Can Suppress Disease-Associated Premature Stop Mutations in the IDUA and P53 cDNAs in a Mammalian Translation System" Jun. 1, 2002, J. Molecular Med. 80(6):367-376.
Keeling et al. "Gentamicin-mediated Suppression of Hurler Syndrome Stop Mutations Restores a Low Level of ?-L-iduronidase Activity and Reduces Lysosomal Glycosaminoglycan Accumulation" Feb. 1, 2001, Hum. Mol. Genet. 10(3):291-299.
Lai et al. "Correction of ATM Gene Function by Aminoglycoside-Induced Read-Through of Premature Termination Codons" Nov. 2, 2004, PNAS USA 101(44):15676-15681.
Lavin "Generating SM(a)RTer Compounds for Translation Termination Suppression in A-T and Other Genetic Disorders" Sep. 1, 2013, Molecular Therapy 21(9):1651-1652.
Lee et al. "Pharmaceutical Therapies to Recode Nonsense Mutations in Inherited Diseases" 2012, Pharmacol. & Therap. 136:227-266.
Callahan et al., "CTLA-4 and PD-1 Pathway Blockade: Combinations in the Clinic," Frontiers in Oncology (Jan. 2015) vol. 4, Article 385, pp. 1-6.
Loudon et al., "Repurposing Amlexanox as a 'Run the Red Light Cure-All' with Readthrough—a 'No Nonsense' Approach to Personalized Medicine," J. Bioanal. Biomed. (2013) vol. 5(4), pp. 79-96.

(56) References Cited

OTHER PUBLICATIONS

Riaz et al., "The Role of Neoantigens in Response to Immune Checkpoint Blockade," International Immunology, vol. 28, No. 8, pp. 411-419.

* cited by examiner

FIG. 1: Ataluren/NMDI Enhances Dual Checkpoint Immunotherapy

METHODS FOR INDUCING AN IMMUNE RESPONSE

CROSS-REFERENCE TO RELATED APPLICATIONS

This application is a continuation of U.S. patent application Ser. No. 16/065,745, filed Jun. 22, 2018, which is a U.S. national stage filing under 35 U.S.C. § 371 of International Application No. PCT/US2016/068591 filed Dec. 23, 2016, which claims priority to U.S. Provisional Patent Application No. 62/387,565, filed Dec. 23, 2015, the disclosures of which are incorporated by reference herein in their entirety.

FIELD OF INVENTION

This invention relates generally to compositions and methods for modulating pathways associated with the regulation of nonsense mediated decay in abnormal cells in order to induce an immune response to them.

BACKGROUND

Despite the progress made in the development of cancer therapeutics over the past two decades, treatments based on inducing the immune system to attack abnormally proliferating cells have had only limited success in slowing tumor progression, including progression to metastatic disease. One reason for this lies in the fact that the naturally occurring response by the immune system to cancer cells is weak, in part because cancer cells do not generally express antigens that the immune system recognizes as foreign. For the most part, conventional cancer vaccines rely on weakly immunogenic antigens expressed on tumor cells in order to bring about an immune response throughout the body. However, even the best cancer vaccines are effective at only temporarily delaying disease progression and very few have been shown capable of reversing it.

As such, there is a particular need for improved compositions and methods for inducing the expression of neoantigens on the surface of cancer cells. Such novel antigens would be capable of bringing about a potent immune response in an individual leading to the destruction and elimination of the cancer cells throughout the individual's body.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

The invention provided herein discloses, inter alia, compositions and methods for generating an immune response in an individual and/or inducing the expression of neoantigens on the surface of abnormal (such as proliferative) cells via promotion of premature termination codon (PTC) readthrough and inhibition of nonsense-mediated decay (NMD) of messenger RNAs (mRNAs) bearing PTCs.

Accordingly, in some aspects, provided herein are methods for generating an immune response in an individual in need thereof comprising administering to the individual 1) an amount of a compound that promotes premature termination codon read-through in an mRNA that has a frameshift mutation resulting in the generation of a premature termination codon; and 2) an amount of a compound that inhibits the nonsense-mediated decay (NMD) of an mRNA that has a frameshift mutation resulting in a premature termination codon (PTC), wherein the amount is sufficient to result in the translation of the mRNA into a protein. In other aspects, provided herein are methods for inducing the expression of one or more neoantigens on the surface of an abnormal cell, the method comprising contacting the cell with 1) a compound that promotes premature termination codon readthrough in an mRNA that has a frameshift mutation resulting in the generation of a premature termination codon; and 2) a compound that inhibits the nonsense-mediated decay (NMD) of an mRNA that has a frameshift mutation resulting in a premature termination codon (PTC), wherein readthrough of the premature termination codon and inhibition of NMD of the mRNA results in the translation of the mRNA into a protein and expression of one or more neoantigens on the surface of the cell. In some embodiments of any of the embodiments disclosed herein, the protein translated from the mRNA with the frameshift mutation is non-functional. In some embodiments, the immune response is mediated by recognition of the processed protein from the translation of the mRNA by immune cells. In some embodiments, the immune cells are T cells or B cells. In some embodiments, the immune response is mediated by a class I or class II major histocompatibility complex (MHC) molecule. In some embodiments of any of the embodiments disclosed herein, the immune response is mediated by T cells. In some embodiments of any of the embodiments disclosed herein, the immune response is mediated by B cells. In some embodiments of any of the embodiments disclosed herein, the T cells are gamma delta T cells, alpha beta T cells or natural killer T cells. In some embodiments of any of the embodiments disclosed herein, the immune response is an inflammatory response. In some embodiments of any of the embodiments disclosed herein, the mRNA is expressed in a proliferative cell. In some embodiments of any of the embodiments disclosed herein, the proliferative cell is a cancer cell. In some embodiments, the cancer is selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia, chronic leukemia; polycythemia vera, lymphoma, multiple myeloma, Waldenstrom's macroglobulinemia, and heavy chain disease. In some embodiments of any of the embodiments disclosed herein, the compound that promotes premature termination codon read-through in an mRNA is a small molecule chemical compound. In some embodiments, the compound that promotes premature termination codon read-through in an mRNA is Ataluren. In some embodiments of any of the embodiments disclosed herein, the compound that inhibits the nonsense-mediated decay (NMD) of an mRNA is not an inhibitory nucleic acid. In some embodiments of any of the embodiments disclosed herein, the compound that inhibits the nonsense-mediated decay (NMD) of an mRNA is a small molecule chemical compound, an antibody, or a non-antibody binding polypeptide. In some embodiments of any of the embodiments disclosed herein, the compound that inhibits the nonsense-mediated decay (NMD) of an mRNA inhibits the function of the UPF3A, UPF3B, UPF1, UPF2, UPF3, eIF4AIII, MLN51, the Y14/MAG0H heterodimer, SMG-1, SMG-5, SMG-6 and/or SMG-7 polypeptides. In some embodiments of any of the embodiments disclosed herein, the method further comprises administration of a compound that inhibits one or more immune checkpoint molecules. In some embodiments, the immune checkpoint molecule is one or more of CTLA4, PD-L1, PD-1, A2AR, B7-H3, B7-H4, or TIM3. In some embodiments, the compound that inhibits one or more immune checkpoint molecules is an antagonistic antibody. In some embodiments, the antagonistic antibody is ipilimumab, nivolumab, pembrolizumab, durvalumab, atezolizumab, tremelimumab, or avelumab. In some embodiments of any of the embodiments disclosed herein, the method further comprises administration of one or more epigenetic modulatory compounds. In some embodiments, the epigenetic modulatory compound is one or more of vorinostat, romidepsin, decitabine; 5-azocytidine, panobinostat, and/or belinostat. In some embodiments of any of the embodiments disclosed herein, the individual is a mammal. In some embodiments, the mammal is a human.

In other aspects, provided herein are methods for generating an immune response in an individual in need thereof comprising administering to the individual 1) an amount of a compound that promotes premature termination codon read-through in an mRNA that has a nonsense mutation resulting in the generation of a premature termination codon; and 2) a compound that inhibits the nonsense-mediated decay (NMD) of an mRNA that has a nonsense mutation, wherein the amount is sufficient to result in the translation of the mRNA into a protein. In further aspects, provided herein are methods for inducing the expression of one or more neoantigens on the surface of an abnormal cell, the method comprising contacting the cell with 1) a compound that promotes premature termination codon read-through in an mRNA that has a nonsense mutation resulting in the generation of a premature termination codon; and 2) a compound that inhibits the nonsense-mediated decay (NMD) of an mRNA that has a nonsense mutation, wherein read-through of the premature termination codon and inhibition of the nonsense-mediated decay (NMD) of an mRNA that has a nonsense mutation results in the translation of the mRNA into a protein and expression of one or more neoantigens on the surface of the cell. In some embodiments of any of the embodiments disclosed herein, the protein translated from the mRNA with the nonsense mutation is not a tumor suppressor gene. In some embodiments of any of the embodiments disclosed herein, the protein translated from the mRNA with the nonsense mutation is not one or more of dystrophin, alpha-L-iduronidase, and/or the cystic fibrosis transmembrane conductance regulator (CFTR) protein. In some embodiments, the immune response is mediated by recognition of the processed protein from the translation of the mRNA by immune cells. In some embodiments, the immune cells are T-cells or B cells. In some embodiments, the immune response is mediated by a class I or class II major histocompatibility complex (MHC) molecule. In some embodiments of any of the embodiments disclosed herein, the immune response is mediated by T cells. In some embodiments of any of the embodiments disclosed herein, the immune response is mediated by B cells. In some embodiments of any of the embodiments disclosed herein, the T cells are gamma delta T cells, alpha beta T cells or natural killer T cells. In some embodiments of any of the embodiments disclosed herein, the immune response is an inflammatory response. In some embodiments of any of the embodiments disclosed herein, the mRNA is expressed in a proliferative cell. In some embodiments of any of the embodiments disclosed herein, the proliferative cell is a cancer cell. In some embodiments, the cancer is selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia, chronic leukemia; polycythemia vera, lymphoma, multiple myeloma, Waldenstrom's macroglobulinemia, and heavy chain disease In some embodiments of any of the embodiments disclosed herein, the method further comprises administration of a compound that inhibits one or more immune checkpoint molecules. In some embodiments, the immune checkpoint molecule is one or more of CTLA4, PD-L1, PD-1, A2AR, B7-H3, B7-H4, or TTM3. In some embodiments, wherein the compound that inhibits one or more immune checkpoint molecules is an antagonistic antibody. In some embodiments, the antagonistic antibody is ipilimumab, nivolumab, pembrolizumab, durvalumab, atezolizumab, tremelimumab, or avelumab. In some embodiments of any of the embodiments disclosed herein, the method further comprises administration of one or more epigenetic modulatory compounds. In some embodiments, the epigenetic modulatory compound is one or more of vorinostat, romidepsin, decitabine, 5-azocytidine, panobinostat, and/or belinostat. In some embodiments of any of the embodiments disclosed herein, the compound that promotes premature termination codon read-through in an mRNA is a small molecule chemical compound. In some embodiments, the compound that promotes premature termination codon read-through in an mRNA is Ataluren. In some embodiments of any of the embodiments disclosed herein, the compound that inhibits the nonsense-mediated decay (NMD) of an mRNA is not an inhibitory nucleic acid. In some embodiments of any of the embodiments disclosed herein, the compound that inhibits the nonsense-mediated decay (NMD) of an mRNA is a small molecule chemical compound, an antibody, or a non-antibody binding polypeptide. In some embodiments of any of the embodiments disclosed herein, the compound that inhibits the nonsense-mediated decay (NMD) of an mRNA inhibits the function of the UPF3A, UPF3B, UPF1, UPF2, UPF3, eIF4AIII, MLN51, the Y14/MAG0H heterodimer, SMG-1, SMG-5, SMG-6 and/or SMG-7 polypeptides. In some embodiments of any of the embodiments disclosed herein, the individual is a mammal. In some embodiments, the mammal is a human.

Each of the aspects and embodiments described herein are capable of being used together, unless excluded either explicitly or clearly from the context of the embodiment or aspect.

DETAILED DESCRIPTION

Figure 1:
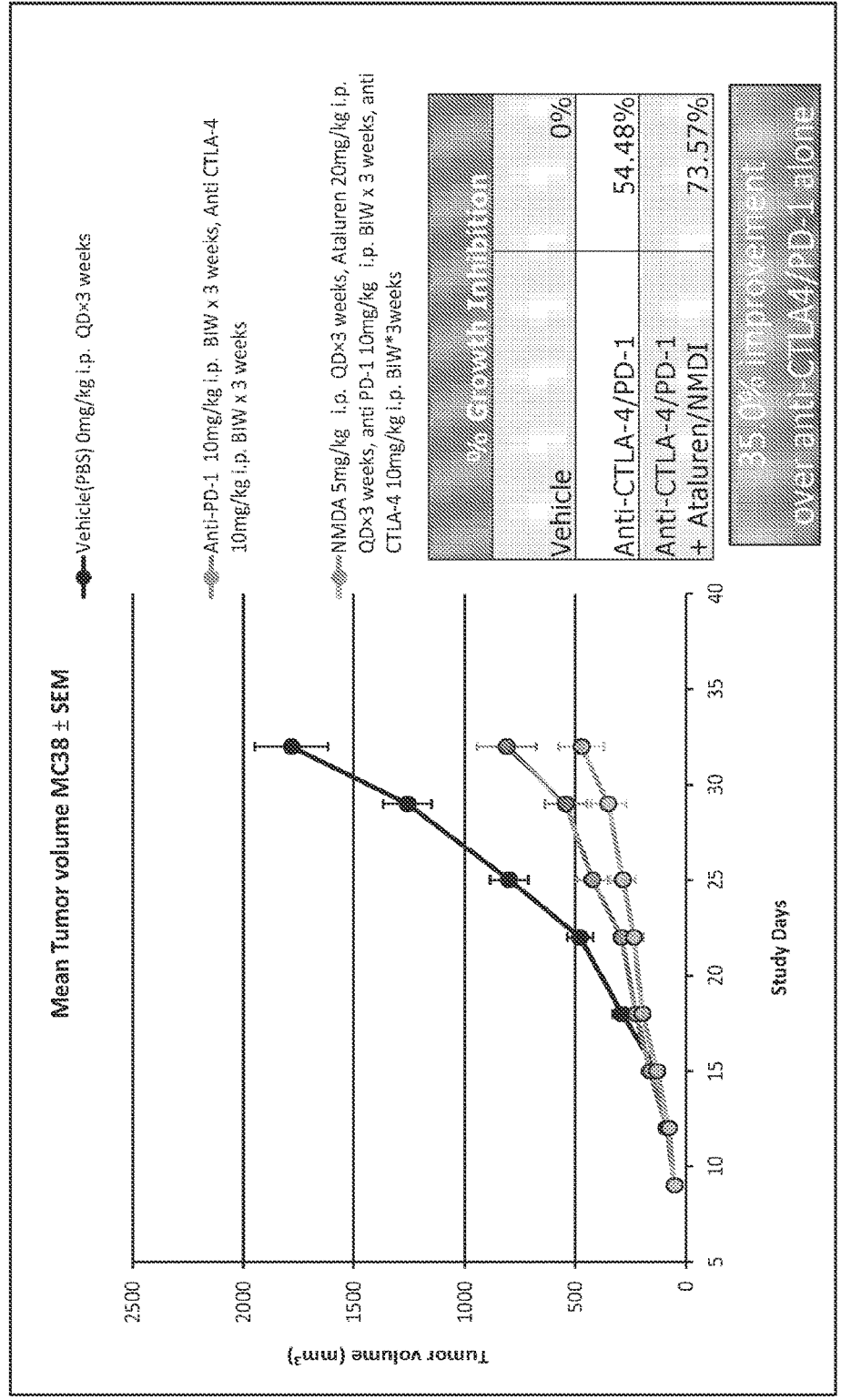
FIG. 1 depicts a graph comparing the effect of administration of PTC124 (Ataluren) and NMDI14 in combination with an anti-PD-1 antibody and an anti-CTLA-4 antibody on tumor volume ($mm^3$).

A major impediment to the efficacy of checkpoint blockade for cancer immunotherapy relates to the scarcity of potent tumor neoantigens expressed by late stage cancers that have undergone extensive immunoediting. This process takes place early in the lifecycle of a tumor, and results in the deletion of populations of tumor cells that expressed immunogenic or strong tumor specific antigens and were therefore targeted by cytotoxic T cells. A mature tumor, therefore, is comprised mainly of tumor cells that have evolved multiple immunoevasion strategies, such as expression of only weak tumor antigens, and are therefore less likely to be effectively targeted by cytotoxic T cells. Despite the recent successes of checkpoint blockade as an immunotherapeutic modality in cancer, the efficacy of these drugs is highly correlated with the availability of robust tumor neoantigens. Notably, tumors in which these drugs are most effective are those with the highest mutational load, such as melanoma and non-small cell lung cancer (NSCLC), both of which carry strong environmentally-induced mutational signatures of UV damage and smoking, respectively.

Efforts in tumor vaccine development in parallel with advances in immunotherapy have led to current approaches in which RNAseq/exome sequencing performed on tumor samples identifies mutated transcripts which are then selected for their ability to serve as robust neoantigens, and are then used as the basis for vaccine development. By virtue of the nature of these mutation detection methods, the overwhelming majority of mRNA species detected are those that contain missense mutations in the coding sequencing, generated by nucleotide transitions and transversions, which lead to either silent or single amino acid substitutions. Although these proteins have the ability to serve as neoantigens, it would be far preferable to identify mutant mRNA species that have more than one amino acid difference, which could then serve as far more robust neoantigens.

A more desirable pool of tumor mRNAs from which to derive robust tumor neoantigens would be those containing premature termination codons (PTC). These mRNA species contain much more deleterious mutations such as insertions, deletions, nonsense mutations and nonstop (delayed termination) mutations. Paradoxically, however, these same PTC-containing species are highly unstable and are rapidly degraded by the nonsense-mediated decay (NMD) pathway, therefore they are generally undetectable in RNA sequences due to their very low abundance or complete absence, and are rarely if ever translated into protein. PTC-containing mRNAs have the potential to encode many divergent amino acids from the wild type sequence due to the shift in reading frame and/or usage of alternate termination codons. If proteins could be transcribed from PTC-containing mRNA species, they would represent a source of extraordinarily potent tumor neoantigens since they can encode proteins with vastly divergent sequences. A therapeutic approach aimed at blocking the NMD pathway and promoting PTC read-through in tumors would allow PTC-containing transcripts to be translated, and strong neoantigens to be expressed in vivo.

Accordingly, this invention provides, inter alia, methods and compositions for generating an immune response in an individual having cells that express one or more messenger RNA (mRNA) molecules bearing a premature termination codon (PTC), by inducing the expression of one or more neoantigens on the surface of those cells. The invention is based, in part, on the inventors' discovery that inhibition of molecular pathways associated with the regulation of nonsense mediated decay (NMD) results in the "read-through" and subsequent translation of mRNAs bearing PTCs into polypeptides having amino acid sequences that vary from the corresponding wild type protein, sometime significantly. Without being bound to theory, proteolysis and presentation of these peptides on the surface of cells via major histocompatibility complex (WIC) molecules can result in a highly antigenic target for attack by components of the immune system, for example, T cells. As will be described further below, not only did a combination of compounds that promote PTC read-through and inhibit NMD effectively inhibit the replication of tumor cells in an in vivo model, the addition of compounds specific for one or more immune checkpoint molecules to the treatment regimen synergistically enhanced the anti-proliferative effect. Thus, aspects of the invention disclosed herein have particular utility for the treatment of diseases characterized by hyperproliferative cells, such as, for example, cancer due to the hypermutable nature of rapidly dividing cells. Cancer cells avoid detection by the immune system in part by displaying only weakly- or non-antigenic peptides on their surface. Accordingly, in one embodiment, the compositions and methods disclosed herein provide an effective way to induce the expression of neoantigens on the surface of cancer cells, thereby rendering them vulnerable to attack by the immune system.

2. General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, NY (Greenfield, ed., 2014), Beaucage et al. eds., *Current Protocols in Nucleic Acid Chemistry*, John Wiley & Sons, Inc., New York, 2000, (including supplements through 2014), *Gene Transfer and Expression in Mammalian Cells* (Makrides, ed., Elsevier Sciences B.V., Amsterdam, 2003), and *Current Protocols in Immunology* (Horgan K and S. Shaw (1994) (including supplements through 2014).

II. Definitions

As used herein, a "premature termination codon" (PTC) or "premature stop codon" refers to the introduction of a stop codon into an mRNA (prior to the endogenous termination codon) as the result of a mutation.

A "nonsense mutation," as used herein, is a point mutation in a sequence of DNA resulting in a PTC, or a nonsense codon, in the transcribed mRNA, and in a truncated, incomplete, and usually nonfunctional protein product. Nonsense mutations are genetic mutations that may underlie a variety of diseases, particularly those that are genetically inherited. In cancer, for example, nonsense mutations are generally acquired or somatic mutations in the tumor. In some embodiments, the nonsense mutation is a somatic mutation. In another embodiment, the nonsense mutation is not a germline mutation.

A "nonstop mutation" is a point mutation in the endogenous termination codon that leads to continued and inappropriate translation of the mRNA into the 3' untranslated region. A nonstop mutation leads to incorporation of an abnormal amino acid sequence and utilization of a downstream termination codon. In some embodiments, the nonstop mutation is a somatic mutation. In another embodiment, the nonstop mutation is not a germline mutation.

A "frameshift mutation" refers to a deletion or insertion of one or more nucleotides within an open reading frame, for example, a single nucleotide or dinucleotide deletion or insertion, such that the reading frame of the coding region is shifted by one or two nucleotides. Thus, the amino acid sequence of a polypeptide translated from an mRNA bearing a frameshift mutation is highly dissimilar to the corresponding wild type sequence. In some embodiments, a frameshift mutation produces a PTC. In some embodiments, the frameshift mutation is a nucleotide or dinucleotide deletion leading to a+1 or +2 frameshift mutation. However, any number of nucleotide deletions can occur provided a frameshift mutation results. Alternatively, the insertion of one or more nucleotides may give rise to a frameshift and such mutations also form part of the present invention. Other genetic modifications which give rise to a frameshift also form part of the present invention, such as a splice site mutation that results in exon skipping or retention of an intronic sequence or change in the nucleotide sequence which leads to translation initiation from a different position or a mutation outside a coding region, such as within an intron or a 5' or 3' untranslated region, which mutation may result in mistranslation and production of a mutant protein. In this type of gene mutation, the mutant protein would be completely mutant amino acid sequences and would contain no wild-type sequences. In some embodiments, a frameshift mutation can lead to a premature termination codon (when it occurs early in the mRNA) or alternatively a delayed termination codon (when it occurs near to the endogenous termination codon. In some embodiments, the frameshift mutation is a somatic mutation. In another embodiment, the frameshift mutation is not a germline mutation.

A "nonfunctional" polypeptide, as used herein, refers to a polypeptide that, due to one or more mutations, is unable to perform a function in a cellular context in comparison to a corresponding non-mutated (wild type) polypeptide. A "functional" polypeptide is a polypeptide that can, at least to some extent, perform a cellular function even though it may have one or more mutated amino acids in comparison to a corresponding non-mutated (wild type) polypeptide.

The term "read-through" herein means to skip over a premature termination codon in ribosomal translation, or to substitute an amino acid, or to suppress degradation of mRNA that comprises a premature termination codon.

As used herein, the term "polypeptides" includes proteins, peptides, fragments of polypeptides, and fusion polypeptides.

The terms "patient" or "individual" are used interchangeably herein, and refer to a subject to be treated. In some embodiments, the individual is a mammal. In other embodiments, the mammal is a human. In some cases, the methods of the invention find use in experimental animals, in veterinary application, and in the development of animal models for disease, including, but not limited to, rodents including mice, rats, and hamsters, and primates.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

III. Compositions

Premature termination codon (PTC) mutations are those in which a base substitution or frameshift mutation changes a sense codon into one of three stop codons (UAA, UAG, or UGA). Studies of yeast, human genetic disorders, and immunoglobulin family gene expression have identified an RNA surveillance mechanism that minimizes the translation and regulates the RNA stability of nonsense RNAs containing such chain termination mutations. This surveillance mechanism is called "nonsense-mediated mRNA decay" ("NMD)," see, e.g., Hentze & Kulozik, *Cell* 96:307-310 (1999); Culbertson, *Trends in Genetics* 15:74-80 (1999); and Li & Wilkinson, *Immunity* 8:135-141 (1998). NMD is a post transcriptional mechanism that is operational in both normal cells (e.g., B and T cells) and cells with genetic mutations (i.e., cells with mutations in genes controlling cellular proliferation).

While many of the proteins involved in NMD are not conserved between species, in *Saccharomyces cerevisiae* (yeast), there are three main factors in NMD: UPF1, UPF2 and UPF3 (UPF3A and UPF3B in humans), that make up the conserved core of the NMD pathway (Behm-Ansmant & Izaurralde, 2006, *Genes & Development* 20 (4): 391-398). All three of these factors are trans-acting elements called up-frameshift (UPF) proteins. In mammals, UPF2 and UPF3 are part of the "exon-exon junction complex" (EJC) bound to mRNA after splicing along with other proteins which also function in NMD. UPF1 phosphorylation is controlled by the proteins SMG-1, SMG-5, SMG-6 and SMG-7.

The process of detecting aberrant transcripts occurs during translation of the mRNA. A popular model for the detection of aberrant transcripts in mammals suggests that during the first round of translation, the ribosome removes the exon-exon junction complexes bound to the mRNA after splicing occurs. If after this first round of translation, any of these proteins remain bound to the mRNA, NMD is activated. Exon-exon junction complexes located downstream of a PTC are not removed from the transcript because the ribosome is released before reaching them. Termination of translation leads to the assembly of a complex composed of UPF1, SMG1 and the release factors, eRF1 and eRF2, on the mRNA. If an EJC is left on the mRNA because the transcript contains a PTC, then UPF1 comes into contact with UPF2 and UPF3, triggering the phosphorylation of UPF1.

In vertebrates, the location of the last exon-junction complex relative to the termination codon usually determines whether the transcript will be subjected to NMD or not. If the termination codon is downstream of or within about 50 nucleotides of the final exon-junction complex then the transcript is translated normally. However, if the termination codon is further than about 50 nucleotides upstream of any exon-junction complexes, then the transcript is down regulated by NMD (Lewis et al., 2003, *Proc. Nat. Acad. Sci. U.S.A.*, 100:189-192). The phosphorylated UPF1 then interacts with SMG-5, SMG-6 and SMG-7, which promote the dephosphorylation of UPF1. SMG-7 is thought to be the terminating effector in NMD, as it accumulates in P-bodies, which are cytoplasmic sites for mRNA decay. In both yeast and human cells, the major pathway for mRNA decay is initiated by the removal of the 5' cap followed by degradation by XRN1, an exoribonuclease enzyme. The other pathway by which mRNA is degraded is by deadenylation from 3'-5'.

Accordingly, without being bound to theory and in one aspect of the invention, there are at least two ways to evade the NMD pathway in order to induce the translation of an mRNA bearing a PTC into a polypeptide: 1) provide a compound that promotes read-through of a PTC, thus ensuring the removal of all EJCs associated with mRNA during the initial round of translation by the ribosome; and/or 2) inhibition of one or more proteins associated with the NMD degradation complex (such as, but not limited to, UPF1, UPF2, UPF3, eIF4AIII, MLN51, the Y14/MAGOH heterodimer, SMG-1, SMG-5, SMG-6 and/or SMG-7).

A. Compounds that Promote PTC Read-Through

Any compound capable of promoting read-through of an mRNA bearing a PTC is suitable for use in the present invention. To date, most reported PTC read-through compounds that are active in mammalian cells have belonged to the aminoglycoside class of antibiotics. Certain types of aminoglycosides can induce ribosomes to read-through PTC mutations via insertion of a random amino acid by a near-cognate transfer RNA (tRNA). The therapeutic potential of aminoglycosides has been evaluated in the laboratory for different genetic models, such as cystic fibrosis (see, e.g., Du et al., 2002, *J. Mol. Med.* 80.595-604), muscular dystrophy (see, e.g., Loufrani et al., 2004, *Arterioscler. Thromb. Vasc. Biol.* 24:671-676), Hurler syndrome (Keeling et al., 2001, *Hum. Mol. Genet.* 10:291-299), cystinosis (Helip-Wooley et al., 2002, *Mol. Genet. Metab.* 75: 128-133), spinal muscular atrophy (Sossi et al., 2001, *Eur. J. Hum. Genet.* 9: 113-120), ataxia-telangiectasia (Lai et al., 2004, *Proc. Natl. Acad. Sci. USA*, 101: 15676-15681), and type 1 Usher syndrome (Rebibo-Sabbah et al., 2007, *Hum. Genet.* 122:373-381). Clinical trials also indicate that aminoglycosides can induce some functional protein production; however, the therapeutic benefits remain uncertain (see, e.g., Politano et al., 2003, *Acta Myol.* 22: 15-21).

A a more efficient nonaminoglycoside read-through compound, ataluren (formerly known as PTC 124), was developed synthetically by screening >800,000 chemicals and analogues using a luciferase-based high-throughput screening (HTS) assay (see, e.g., Welch et al., 2007, *Nature.* 447: 87-91). A phase-I clinical study in cystic fibrosis confirmed that ataluren is generally well tolerated and appears to have more efficient read-through activity than aminoglycosides (Hirawat et al., 2007, *J. Clin. Pharmacol.* 47:430-444). Moreover, PTC 124 does not induce ribosomal read-through of normal stop codons.

Accordingly, in one embodiment, the compound that promotes PTC read-through is a 1,2,4-oxadiazole benzoic acid compound of formula I:

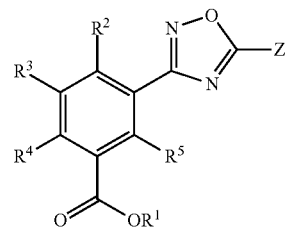

or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstituted alkyl, substituted or unsubstituted alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —$(CH_2CH_2)_nOR^6$ or any biohydrolyzable group;

$R^2$, $R^3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $N(R^7)_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or $CF_3$; and n is an integer from 1 to 7.

In a further embodiment, the compound that promotes PTC read-through is 3-[5-(2-Fluorophenyl)-1,2,4-oxadiazol-3-yl]benzoic acid.

In some aspects, the compound that promotes PTC read-through is a small molecule. Small molecules are preferably organic molecules other than binding polypeptides or antibodies as defined herein. Organic small molecules may be identified and chemically synthesized using known methodology (see, e.g., PCT Application Publication Nos. WO 00/00823 and WO 00/39585). Organic small molecules are usually less than about 2000 Daltons in size, alternatively less than about 1500, 750, 500, 250 or 200 Daltons in size, wherein such organic small molecules that are capable of promoting PTC read-through as described herein may be identified without undue experimentation using well known techniques. In this regard, it is noted that techniques for screening organic small molecule libraries for molecules that are capable of promoting PTC read-through are well known in the art (see, e.g., U.S. Patent Application Publication Nos. 2004/0214193 and 2003/0049666; and International Patent Application Publication No. WO 2001/044516, the disclosures of which are incorporated by reference herein).

Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of promoting PTC read-through or mediating a biological activity of interest (such as, but not limited to, translation of an mRNA bearing a PTC).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclo-condensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al, (1993), *Proc. Natl. Acad. Sci. USA* 90: 10700-10704; and PCT Application Publication No. WO 97/15390, the disclosures of which are incorporated by reference herein.

In certain embodiments, the compounds for promoting PTC read-through for use in the methods disclosed herein are

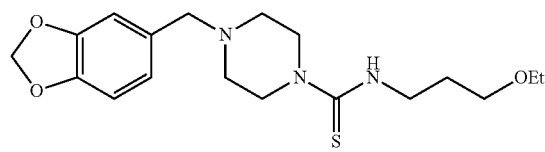

GJ071

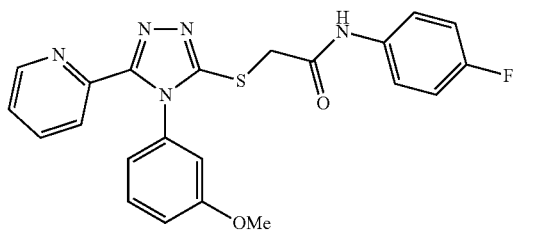

GJ072

In some embodiments, the compound for promoting PTC read-through suitable for use in any of the methods disclosed herein is an aminoglycoside such as, without limitation, amikacin, G418 (geneticin), gentamicin, or paromomycin. In other embodiments, the PTC read-through compound is an aminoglycoside derivative such as, without limitation, NB54, NB74, NB84, or TC007. In further embodiments, the compound for promoting PTC read-through is a non-aminoglycoside such as, without limitation, negamycin or tylosin, (see also Bidou et al., 2012, *Trends Molec. Med.* 18(11):679-88; McKinney et al., 2015, *ACS Med. Let*, 6:930-955; and Du et al., 2009, *J. Exp. Med.*, 206(10):2285-97, incorporated by reference herein).

In further embodiments, the compounds for promoting PTC read-through for use in the methods disclosed herein are

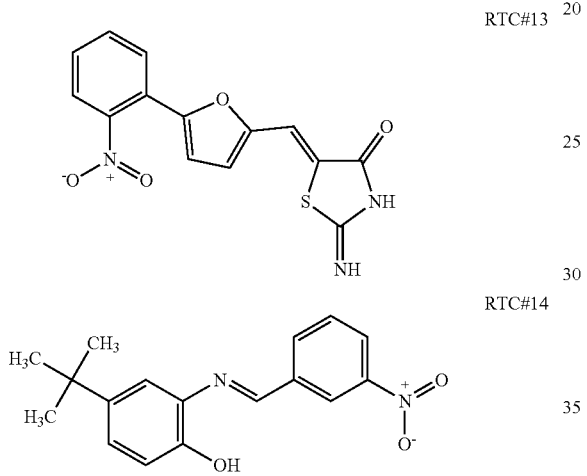

In yet other embodiments, the compounds for promoting PTC read-through for use in the methods disclosed herein can be negamycin derivatives, such as, without limitation

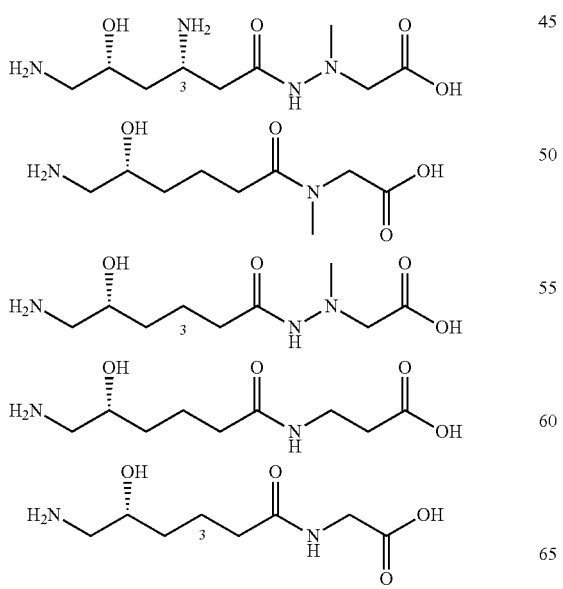

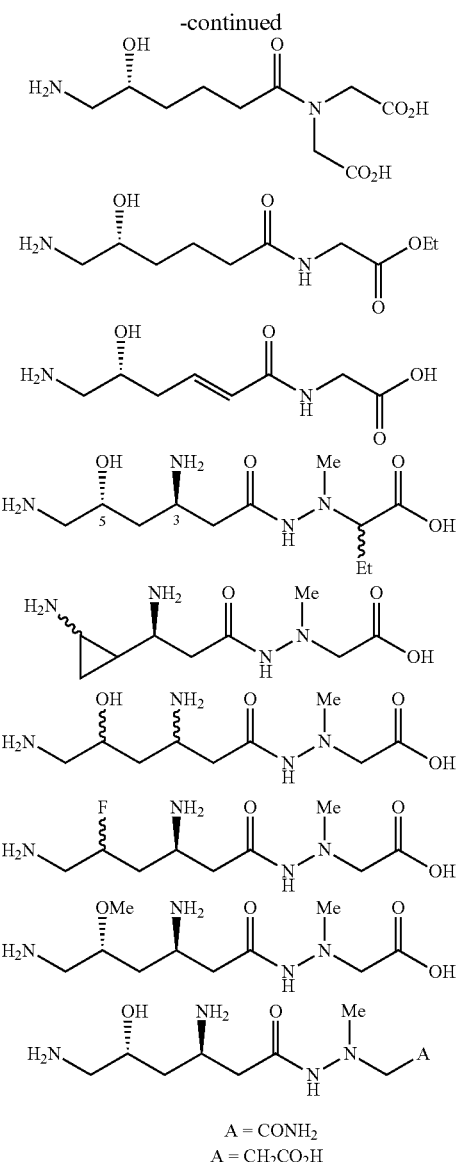

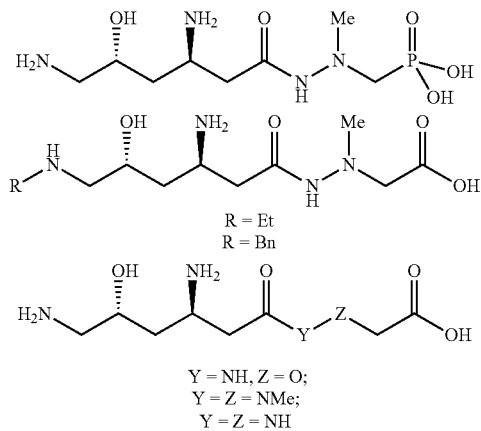

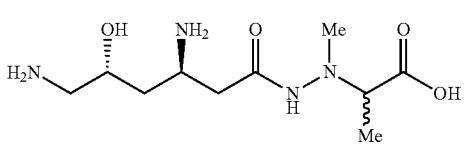

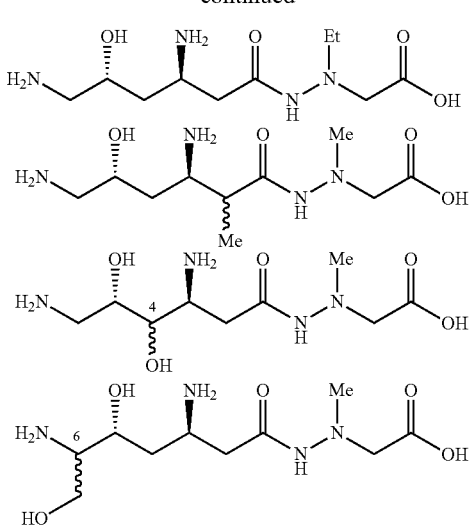

Further PTC read-through drugs appropriate for use in the methods disclosed herein include, without limitation, isepamicin, tobramycin, RTC #1, RTC #2, RTC #3, RTC #4, RTC #7, RTC #9, RTC #10, RTC #11, RTC #16, RTC #17, clitocin, macrolide spiramycin, macrolide josamycin, macrolide tylosin, NB30, streptomycin, hygromycin, puromycon, lividomycin, TC001, TC003, TC032, JL022, JL023, hygromycin B, kanamycin A, kanamycin B and its "JL" derivatives, neomycin and its "TC" derivatives, paroamine and its synthetic derivatives, paromomycin and its "NB" derivatives, or oleandomycon (see Lee & Dougherty, 2012, *Pharmacol & Therap.*, 136:227-66, the disclosure of which is incorporated by reference herein). Other PTC-readthrough drugs include negamycin and gentamycin.

Other compounds suitable for promoting PTC readthrough in for use in the instant invention can be found in U.S. Patent Application Publication Nos. 2015/0274674, 2015/0051251, 2013/0217717, 2012/0087896, 2011/0046136, 2011/0003843, 2010/0093867, 2008/0207538, 2007/0203123, 2006/0166926, and 2006/0167263; International Patent Application Publication Nos. WO 2015/134711, WO 2015/109248, WO 2013/142346, WO 2012/016930, WO 2008/101935, WO 2004/009558, WO 2004/009610, WO 2004/009533, and WO 2014/055644; and U.S. Pat. Nos. 8,163,782 and 6,992,096, the disclosures of each of which are incorporated by reference herein in their entireties.

B. Compounds that Inhibit the NMD Complex

In further aspects the compound modulates the expression and function of one or more molecules associated with nonsense mediated decay of one or more proteins associated with the NMD degradation complex. As used herein, the phrase "NMD degradation complex" refers to any one of the intracellular proteins that participates in NMD of an mRNA bearing a PTC (such as, but not limited to, one or more of UPF1, UPF2, UPF3, UPF3BI, RNPS1, eIF4AIII, MLN51, the Y14/MAG0H heterodimer, RENT1, RENT2, SMG-1, SMG-5, SMG-6 and/or SMG-7). As such, the compound inhibits the function of one or more NMD degradation complex proteins, thereby allowing a PTC-bearing mRNA to be translated into a polypeptide.

Candidate compounds can be, without limitation, small molecule chemical compounds (such as any of the small molecules described above), antibodies, proteins, or any combination thereof. In one embodiment, the compound is not an inhibitory nucleic acid (such as, but not limited to, an antisense oligonucleotide or a small inhibitory RNA (siRNA)). In another embodiment, the compound is not any of the compounds disclosed in U.S. Patent Application Publication No. 2013/0224237.

1. Antibodies

In some aspects, the compound binds (such as preferentially binds) to a one or more NMD degradation complex proteins (such as, but not limited to, UPF1, UPF2, UPF3, UPF3BI, RNPS1, eIF4AIII, MLN51, the Y14/MAG0H heterodimer, RENT1, RENT2, SMG-1, SMG-5, SMG-6 and/or SMG-7) and is an antibody. In some embodiments, the antibodies are NMD degradation complex protein antagonists and can inhibit NMD.

Variants of antibodies can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Nucleic acid molecules encoding amino acid sequence variants of the antibody can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

Fc region variants with altered (i.e. improved or diminished) Clq binding and/or Complement Dependent Cytotoxicity (CDC) are described in International Patent Application Publication No.: WO99/51642 (incorporated herein by reference). Such variants may comprise an amino acid substitution at one or more amino acid positions of the Fc region. See, also, Duncan & Winter, *Nature* 322:738-40 (1988); U.S. Pat. Nos. 5,648,260; 5,624,821; and International Patent Application Publication No.: WO94/29351 concerning Fc region variants, the disclosures of each of which are incorporated by reference herein.

2. Non-Antibody Binding Polypeptides

In some aspects, the compound binds (such as preferentially binds) to a one or more NMD degradation complex proteins (such as, but not limited to, UPF1, UPF2, UPF3, UPF3BI, RNPS1, eIF4AIII, MLN51, the Y14/MAG0H heterodimer, RENT1, RENT2, SMG-1, SMG-5, SMG-6 and/or SMG-7) and is a non-antibody binding polypeptide. In some embodiments, the non-antibody binding polypeptide is a NMD degradation complex protein antagonist and can inhibit NMD.

Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding to a target, such as any component of the NMD degradation complex discussed herein.

Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Application Publication Nos. WO 84/03506 and WO84/03564; Geysen et al, *Proc. Natl. Acad. Sci. U.S.A.*, 81:3998-4002 (1984); Geysen et al, *Proc. Natl. Acad. Sci. U.S.A.*, 82: 178-182 (1985); Geysen et al., *J. Immunol. Meth,* 102:259-274 (1987); Clackson, T. et al, (1991) *Nature,* 352: 624; Kang, A. S. et al., (1991) *Proc. Natl. Acad. Sci. USA,* 88:8363, and Smith, G. P. (1991) *Current Opin. Biotechnol,* 2:668, the disclosures of each of which are incorporated by reference herein.

Methods for generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323, the disclosures of each of which are incorporated by reference herein.

Binding polypeptides can be modified to enhance their inhibitory and/or therapeutic effect (including, for example, enhanced affinity, improved pharmacokinetic properties such as half-life, stability, and clearance rate, reduced toxicity, etc.). Such modifications include, without limitation, glycosylation, pegylation, substitution with non-naturally occurring but functionally equivalent amino acid, linking groups, etc.

C. Pharmaceutical Compositions

Also provided herein are pharmaceutical compositions comprising any of the compounds that promote PTC read-through and compounds that inhibit the NMD complex disclosed herein. The pharmaceutical compositions of the invention may include one or more of tablets, capsules, granules, powder, pellets, caplets, minitablets, lozenges, capsule filled with minitablets and/or pellets, multi-layer tablets, granules for suspension, granules or powder filled in a sachet. In other embodiments, the composition of the present invention can be coated to give film-coated tablets.

The composition of the invention may be prepared by mixing pharmaceutically excipients and granulating them with aqueous or alcoholic solution of compounds that promote PTC read-through and compounds that inhibit the NMD complex along with sugars optionally with other pharmaceutically acceptable excipients. The granules may be dried and lubricated and converted into a suitable dosage form.

The stable solid pharmaceutical compositions of compounds that promote PTC read-through and compounds that inhibit the NMD complex or pharmaceutically acceptable salts thereof may be prepared by processes known to a person having ordinary skill in the art of pharmaceutical technology such as direct compression, wet or dry granulation, slugging, hot melt granulation, hot melt extrusion, fluidized bed granulation, extrusion-spheronization, spray drying and solvent evaporation. In an embodiment, the stable composition of compounds that promote PTC read-through and compounds that inhibit the NMD complex or pharmaceutically acceptable salts thereof are prepared by dry/wet granulating the compound(s) with one or more sugars and one of more pharmaceutically acceptable excipients, and optionally mixing the granules with other excipients.

Pharmaceutically acceptable excipients may include one or more binders, fillers, lubricants, solubilizers, stabilizers, disintegrants, glidants, and the like.

Suitable "diluents" may include one or more of lactose, microcrystalline cellulose, calcium phosphate, dextrin, dextrose, dextrates, mannitol, sorbitol, sucrose, and the like. In particular, the diluents are lactose and microcrystalline cellulose. The diluent may be present in the extragranular and/or intragranular portions of the composition.

Suitable "disintegrants" may include one or more of crospovidone (polyplasdone), low substituted hydroxypropyl cellulose, carmellose, sodium carboxystarch, calcium carmellose, corn starch, partially-alphatized starch, sodium croscarmellose, sodium starch glycolate, and the like. In particular, the disintegrant is crospovidone. The disintegrant may be present in extragranular and/or intragranular portion of the composition.

Suitable "binders" may include one or more of hydroxypropyl cellulose, hydroxypropylmethyl cellulose, polyvinyl pyrrolidone (povidone K30), polyvinyl alcohol, partial saponificates of these, starch, and the like. In particular, the binder is polyvinyl pyrrolidone.

Suitable "solubilizers" may include one or more of poloxamer, polyethylene glycols, polysorbates, sodium lauryl sulfate, glyceryl monostearate, glyceryl monooleate, lecithin, polyoxythylene alkyl esters, polyoxyethylene castor oil derivatives, polyoxyethylene fatty acid esters, and the like. In particular, the solubilizers are poloxamer and glyceryl monooleate.

Suitable "stabilizers" may include one or more of citric acid, tartaric acid, fumaric acid, maleic acid, vitamin E acetate and the like. In particular, the stabilizer is vitamin E acetate.

Suitable "lubricants/glidants" includes one or more of magnesium stearate, stearic acid, palmitic acid, calcium stearate, zinc stearate, sodium stearyl fumarate, glyceryl behenate, talc, and the like.

Any of the compounds for promoting PTC read-through and compounds that inhibit the NMD complex according to the present invention may be formulated in conventional manner using one or more pharmaceutically acceptable carriers or excipients. In some embodiments, multiple routes of administration can be used for drug administration in a given treatment regimen. For example, a compound for promoting PTC read-through can be administered orally while a compound for inhibiting NMD can be administered intravenously. Thus, the compound for use according to the invention may for example be formulated for one or more of oral, sub-lingual, buccal, parenteral, rectal, vaginal, or intranasal administration or in a form suitable for administration by inhalation or insufflation (either through the mouth or nose) or in a form suitable for topical administration, preferably for local application in the eye. In another embodiment, the compound for promoting PTC read-through and compound that inhibit the NMD complex is formulated for topical or subcutaneous administration.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds for promoting PTC read-through and/or inhibiting the NMD complex for use according to the invention may be formulated for parenteral administration by injection, conveniently intravenous, intramuscular, intratumoral, or subcutaneous injection, for example by bolus injection or continuous intravenous infusion. Formulations for injection may be presented in unit dosage form e.g. in ampoules or in multi-dose containers, optionally with an added preservative. The compositions for parenteral administration may take such forms as suspensions, solutions or emulsions in oily or aqueous vehicles, and may contain formulatory agents such as suspending, stabilizing and/or dispersing agents. Alternatively, the active ingredient may be in dry form such as a powder, crystalline or freeze-dried solid for constitution with a suitable vehicle, e.g. sterile pyrogen-free water or isotonic saline before use. They may be presented, for example, in sterile ampoules or vials.

The compounds for promoting PTC read-through and inhibiting the NMD complex for use according to the invention may also be formulated in rectal compositions such as suppositories or retention enemas, e.g. containing conventional suppository bases such as cocoa butter or other glyceride.

Tablets for sub-lingual administration may be formulated in a conventional manner.

For intranasal administration the compounds for promoting PTC read-through and inhibiting the NMD complex for use according to the invention may be used, for example, as a liquid in the form of, for example, a solution, suspension or emulsion, presented in the form of a spray or drops, or as a powder. Preferably the preparation for intranasal administration is delivered in the form of a spray or aerosol from an insufflator or from a pressurized pack or nebulizer with the use of a suitable propellant.

For administration by inhalation the compounds for promoting PTC read-through and inhibiting the NMD complex for use according to the invention can be conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For topical administration the pharmaceutical compositions may be liquids, for example solutions, suspensions or emulsions (such as nanoparticle- or liposome-containing emulsions) presented in the form of creams, gels, lotions, foams or drops suitable for local application to the eye.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

IV. Methods of the Invention

In some aspects, provided herein are methods for generating an immune response in an individual in need thereof and/or methods inducing the expression of one or more neoantigens on the surface of an abnormal cell. NMD is an evolutionary conserved mRNA surveillance pathway in eukaryotic cells that detects and eliminates mRNAs harboring premature termination codons (PTCs). Without wishing to be bound by theory, upregulation of gene expression when NMD is inhibited in tumor cells will translate into a therapeutically useful enhancement of tumor antigenicity, namely that the new products will function as effective tumor antigens, capable of eliciting an immune response which will contribute to tumor rejection. Inhibition will be accomplished by administering an effective amount of one or both of the compounds for promoting PTC read-through and inhibition of the NMD degradation complex described above to an individual in need thereof. In one embodiment, the protein translated from the mRNA following PTC read-through and inhibition of the NMD degradation complex is a non-functional protein. An effective amount can result in the functionality as described below and herein.

In some embodiments, the amount of a compound for promoting PTC read-through and inhibition of the NMD degradation complex administered to the individual is included in any of the following ranges: about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, about 250 to about 300 mg/kg, about 300 to about 350 mg/kg, about 350 to about 400 mg/kg, about 400 to about 450 mg/kg, or about 450 to about 500 mg/kg. In some embodiments, the amount of a telomerase inhibitor in the therapeutically effective amount administered to the individual (e.g., a unit dosage form) is in the range of about 5 mg to about 500 mg, such as about 30 mg to about 300 mg or about 50 mg to about 200 mg or about 10 mg to about 100 mg.

In other embodiments, the concentration of the compound for promoting PTC read-through and inhibition of the NMD degradation complex administered to the individual is dilute (about 0.1 mg/ml) or concentrated (about 200 mg/ml), including for example any of about 0.1 to about 200 mg/ml, about 0.1 to about 180 mg/ml, about 0.1 to about 160 mg/ml, about 0.1 to about 140 mg/ml, about 0.1 to about 120 mg/ml, about 0.1 to about 100 mg/ml, about 0.1 to about 80 mg/ml, about 0.1 to about 60 mg/ml, about 0.1 to about 40 mg/ml, about 0.1 to about 20 mg/ml, about 0.1 to about 10 mg/ml about 2 to about 40 mg/ml, about 4 to about 35 mg/ml, about 6 to about 30 mg/ml, about 8 to about 25 mg/ml, about 10 to about 20 mg/ml, about 12 to about 15 mg/ml, or any of about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2 mg/ml, 2.1 mg/ml, 2.2 mg/ml, 2.3 mg/ml, 2.4 mg/ml, or 2.5 mg/ml.

In some embodiments, the concentration of the compound for promoting PTC read-through and inhibition of the NMD degradation complex is at least about any of 0.1 mg/kg, 0.2 mg/kg, 0.3 mg/kg, 0.4 mg/kg, 0.5 mg/kg, 1.3 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 33.3 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, 80 mg/kg, 81 mg/kg, 82 mg/kg, 83 mg/kg, 84 mg/kg, 85 mg/kg, 86 mg/kg, 87 mg/kg, 88 mg/kg, 89 mg/kg, 90 mg/kg, 91 mg/kg, 92 mg/kg, 93 mg/kg, 94 mg/kg, 95 mg/kg, 96 mg/kg, 97 mg/kg, 98 mg/kg, 99 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 240 mg/kg, or 250 mg/kg.

In further embodiments, treatment with one or more compounds for promoting PTC read-through and inhibition of the NMD degradation complex according to any of the methods disclosed herein results in at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% decrease in tumor size compared to tumors that are not treated with one or more compounds for promoting PTC read-through and inhibition of the NMD degradation complex.

In some embodiments treatment with one or more compounds for promoting PTC read-through and inhibition of the NMD degradation complex according to any of the methods disclosed herein exhibit at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% any of CD4+, CD8+, CD3+, and/or CD45+ effector T cell responses (e.g. intratumoral T-cell infiltration) compared to T-cell responses in tumors that are not treated with one or more compounds for promoting PTC read-through and inhibition of the NMD degradation complex.

In another embodiment, treatment with one or more compounds for promoting PTC read-through and inhibition of the NMD degradation complex according to any of the methods disclosed herein results in at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% tumor inhibitory effect compared to individuals that are not treated with one or more compounds for promoting PTC read-through and inhibition of the NMD degradation complex.

A. Generation of an Immune Response

The immune response elicited by the methods described herein is mediated by recognition of a processed protein generated from the translation of a PTC-containing mRNA by immune cells. In some embodiments, the immune cells are T cells or B cells, which are the major types of lymphocytes derived from hematopoietic stem cells in the bone marrow. B cells are involved in the humoral immune response, whereas T cells are involved in cell-mediated immune response. Both B cells and T cells carry receptor molecules that recognize specific targets. T cells recognize a "non-self target, such protein translated from an mRNA containing a PTC caused by a nonsense or frameshift mutation, after antigens have been processed and presented in combination with a major histocompatibility complex (MEW) molecule. There are two major subtypes of T cells: the killer T cell and the helper T cell. Killer T cells only recognize antigens coupled to Class I MHC molecules, while helper T cells only recognize antigens coupled to Class II MHC molecules. These two mechanisms of antigen presentation reflect the different roles of the two types of T cell. A third, minor, subtype are the y5 T cells that recognize intact antigens that are not bound to MHC receptors (Holtmeier & Kabelitz, (2005), *Chemical Immunology and Allergy*, 86:151-83).

Accordingly, in any of the methods disclosed herein, the immune response can be mediated by either B cells or T cells and the novel antigen presented by either Class I MHC molecule or a Class II MHC molecule. For example, Killer T cells are a sub-group of T cells that kill cells that are damaged or dysfunctional. Killer T cells are activated when their T cell receptor (TCR) binds to this specific antigen in a complex with the MHC Class I receptor of another cell. The T cell then travels throughout the body in search of cells where the MHC I receptors bear this antigen. When an activated T cell contacts such cells, it releases cytotoxins, such as perforin, which form pores in the target cell's plasma membrane, allowing ions, water and toxins to enter. T cell activation is tightly controlled and generally requires a very strong MHC/antigen activation signal, or additional activation signals provided by "helper" T cells.

With respect to B cells, these cells identify a target when antibodies on its surface bind to a specific foreign antigen. This antigen/antibody complex is taken up by the B cell and processed by proteolysis into peptides. The B cell then displays these antigenic peptides on its surface MHC class II molecules. This combination of MHC and antigen attracts a matching helper T cell, which releases lymphokines and activates the B cell. As the activated B cell then begins to divide, its offspring (plasma cells) secrete millions of copies of the antibody that recognizes this antigen. These antibodies circulate in blood plasma and lymph, bind to pathogens expressing the antigen and mark them for destruction by complement activation or for uptake and destruction by phagocytes.

Whether or not a given compound elicits an immune response when administered in accordance with the methods disclosed herein can be measured by any means known in the art including, without limitation, flow cytometric enumeration, CD4 and CD8 effector T cell responses, as well as $T_{reg}$ responses.

B. Abnormal Cells

In some aspects of the methods disclosed herein, the expression of one or more novel antigens is induced on the surface of an abnormal cell. In certain embodiments, the abnormal cell is a hyperproliferative cell, such as cancer.

Cancers that can be prevented and/or treated by the compositions and methods of the present invention include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, merkel cell tumors, cervical cancer, testicular tumor, lung carcinoma, small cell lung carcinoma, bladder carcinoma, epithelial carcinoma, glioma, astrocytoma, medulloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

C. Checkpoint Inhibitors

In some embodiments of any of the methods disclosed herein, the method further comprises administration of one or more compounds that inhibit one or more immune checkpoint molecules. Immune checkpoints are molecules in the immune system that either turn up a signal (co-stimulatory molecules) or turn down a signal. Checkpoint inhibitors are designed to overcome one of the primary ways a cancer cell evades detection by the immune system. T lymphocytes routinely monitor cells for signs of disease. If an antigen on the surface of a cell suggests the cell is abnormal, the T cell will initiate an immune response that includes increasing the expression of additional molecules to prevent the immune response from damaging normal tissues in the body. These molecules are known as immune checkpoints.

Cancer cells often use immune checkpoint molecules to evade or suppress attack by the immune system. Thus, expression of immune checkpoint molecules on the surface of cancers cells prevents immune cells such as T cells from recognizing them as "foreign" or "abnormal." Consequently, checkpoint inhibitors are compounds which block inhibitory immune checkpoint molecules leading to the activation of the immune system via T cell recognition.

Inhibitory checkpoint molecules have been increasingly considered as new targets for cancer immunotherapies due to the effectiveness of two checkpoint inhibitor drugs that were initially indicated for advanced melanoma-ipilimumab (Yervoy™; a monoclonal antibody that works to activate the immune system by targeting CTLA-4), and pembrolizumab (Keytruda™; a humanized antibody that targets the programmed cell death 1 (PD-1) receptor). Another checkpoint inhibitor known as nivolumab (Opdivo™) blocks the interaction between PD-1 and programmed cell death ligand 1 (PD-L1) which prevents inhibition of an immune response.

Any molecule capable of inhibiting one or more immune checkpoint molecules can be used in the methods disclosed herein. These include, without limitation, antibodies or functional fragments thereof, inhibitory polypeptides, small molecule chemical compounds, and/or inhibitory nucleic acids (such as, but not limited to, antisense oligonucleotides, small inhibitory RNAs (siRNAs), small hairpin RNAs (shRNAs), and/or catalytic nucleic acids such as ribozymes). Immune checkpoint molecules suitable for targeting by checkpoint inhibitors for use in any of the methods disclosed herein include, without limitation, one or more of the adenosine $A_{2A}$ receptor (A2AR), B7-H3 (a.k.a. CD276; e.g., MGA271), cytotoxic T-lymphocyte-associated protein 4 (CTLA4; a.k.a. CD152; e.g., ipilimumab; AGEN-1884 (Agenus)), programmed cell death ligand 1 (PD-L1; a.k.a. CD274; e.g., MDX-1105 (Bristol Myers Squibb), WBP-3155 (C-stone), LY3300054 (Eli Lilly)), programmed cell death protein 1 (PD-1; a.k.a. CD279; e.g., pembrolizumab, SHR-1210 (Incyte), STI-A1110 (Sorrento), REGN2810 (Regeneron), CT-011 (pidilizumab; Curetech), PDR-001 (Novartis), BGB-A317 (BeiGene), TSR-042 (Tesaro), ENUMC-8 (Enumeral), MGD-013 (Macrogenics; bispecific antibody for PD1 and Lag3), B7-H4 (a.k.a. VTCN1), T-cell immunoglobulin and mucin-domain containing-3 (TIM3; a.k.a. HAVCR2), B and T Lymphocyte Attenuator (BTLA; a.k.a. CD272), indoleamine-pyrrole 2,3-dioxygenase (IDO), killer-cell immunoglobulin-like receptors (KIRs; e.g., lirilumab), lymphocyte-activation gene 3 (LAG-3; e.g., BMS- 986016), T cell immunoreceptor with Ig and ITIM domains (TIGIT; a.k.a. WUCAM and Vstm3), ILT-3, ILT-4, and/or V-domain Ig suppressor of T cell activation (VISTA).

In some embodiments, the checkpoint inhibitor is an antagonistic antibody, such as, but not limited to, one or more of ipilimumab (Bristol-Myers Squibb), nivolumab (Bristol-Myers Squibb), Pembrolizumab (Merck) durvalumab (Medimmune), atezolizumab (Genentech/Roche), tremelimumab (Medimmune), and/or avelumab (Pfizer).

While antagonistic antibodies such as these have shown some promise for the treatment of cancers, administration of monoclonal antibodies to individuals has also been associated with adverse events and severe side effects due to unwanted immune reactions. Specifically, administration of monoclonal antibodies carries the risk of immune reactions such as acute anaphylaxis, serum sickness and the generation of antibodies. In addition, there are numerous adverse effects associated with monoclonal antibodies related to their specific targets, including infections and cancer, autoimmune disease, and organ-specific adverse events such as cardiotoxicity, hepatitis, pneumonitis, and colitis. It is often the case that individuals undergoing immune checkpoint therapy are administered more than one monoclonal antibody in order to target multiple immune checkpoint proteins at the same time. Unfortunately, the risk of side effects and toxicities increases exponentially with the number of monoclonal antibodies administered to an individual as part of a treatment regimen. As such, a therapeutic regimen that is more or as effective with respect to its ability to inhibit tumor growth as those which currently use multiple monoclonal antibodies to target immune checkpoint proteins yet which does not result in the adverse effects associated with administration of multiple monoclonal antibodies is greatly needed.

As will be discussed further below, in some embodiments, disclosed herein are methods for inhibiting tumor growth in an individual by administering a combination of one or more compounds for promoting PTC read-through and inhibition of nonsense mediated decay and one or more compounds (such as an antibody, e.g. a monoclonal antibody) that inhibits an immune checkpoint protein. The combination of a PTC read-through-promoting/NIVID inhibiting compound added to an immune checkpoint inhibitor compound are as effective or are more effective in inhibiting tumor growth as compared to a combination of two or more antibody-based immune checkpoint inhibitory therapies administered without a combination of one or more compounds for promoting PTC read-through and inhibition of nonsense mediated decay. Additionally, administration of a combination of one or more compounds for promoting PTC read-through and inhibition of nonsense-mediated decay and compound that inhibits an immune checkpoint protein according to the methods described herein results in decreased side effects and adverse events (for example any of about 10%, 20%, 30%, 40%, 50%, 60%, 70%, 80%, 90%, or 100% decreased side effects and adverse events, including all values falling in between these percentages) compared to administration of two or more antibody-based immune checkpoint inhibitory therapies (for example, the combination of anti-PD-1 and anti-CTLA-4 antibodies) alone.

In another embodiment, one or more compounds for promoting PTC read-through and one or more compounds that inhibit nonsense-mediated decay in combination with one or more compounds that inhibit one or more immune checkpoint proteins administered according to any of the methods disclosed herein provide at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% tumor inhibitory effect compared to tumors that are not treated with one or more compounds for promoting PTC read-through and one or more compounds that inhibit nonsense-mediated decay in combination with one or more compounds that inhibit one or more immune checkpoint proteins. In one embodiment the PTC read-through inhibitor is Ataluren (PTC124) and the compound that inhibits nonsense-mediated decay is NMDI14. In another embodiment, the PTC read-through inhibitor (e.g., Ataluren) and the compound that inhibits nonsense-mediated decay (e.g., NMDI14) is administered in combination with an antibody to PD-1. In another embodiment, the PTC read-through inhibitor (e.g., Ataluren) and the compound that inhibits nonsense-mediated decay (e.g., NMDI14) is administered in combination with an antibody to CTLA-4. In a further embodiment, the combination of a PTC read-through inhibitor (e.g., Ataluren) and the compound that inhibits nonsense-mediated decay (e.g., NMDI14) and a single compound that inhibits an immune checkpoint protein (e.g., an anti-PD-1 antibody or an anti-CTLA-4 antibody) is as effective or more effective in inhibiting tumor growth as compared to a combination of two or more compounds that inhibit an immune checkpoint protein (e.g., a combination of an anti-PD-1 antibody and an anti-CTLA-4 antibody) alone.

In a further embodiment, one or more compounds for promoting PTC read-through and one or more compounds that inhibit nonsense-mediated decay in combination with two or more compounds that inhibit one or more immune checkpoint proteins administered according to any of the methods disclosed herein provide at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% tumor inhibitory effect compared to tumors that are not treated with one or more compounds for promoting PTC read-through and one or more compounds that inhibit nonsense-mediated decay in combination with two or more compounds that inhibit one or more immune checkpoint proteins. In one embodiment the PTC read-through inhibitor is Ataluren (PTC124) and the compound that inhibits nonsense-mediated decay is NMDI14. In another embodiment, the PTC read-through inhibitor (e.g., Ataluren) and the compound that inhibits nonsense-mediated decay (e.g., NMDI14) is administered in combination with an antibody to PD-1 and an antibody to CTLA-4.

In another embodiment, one or more compounds for promoting PTC read-through (e.g., Ataluren) and one or more compositions for inhibition of nonsense-mediated decay (e.g., NMDI14) administered in combination one or more compounds that inhibit one or more immune checkpoint proteins (e.g., anti-PD-1 and/or anti-CTLA-4) according to any of the methods disclosed herein provide at least about a 15%, 16%, 17%, 18%, 19%, 20%, 21%, 22%, 23%, 24%, 25%, 26%, 27%, 28%, 29%, 30%, 31%, 32%, 33%, 33.3%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% tumor inhibitory effect compared to tumors that are not treated with one or more compounds for promoting PTC read-through (e.g., Ataluren) and one or more compositions for inhibition of nonsense-mediated decay (e.g., NMDI14) administered in combination one or more compounds that inhibit one or more immune checkpoint proteins (e.g., anti-PD-1 and/or anti-CTLA-4).

D. Epigenetic Modulatory Compounds

In some embodiments of any of the methods disclosed herein, the method further comprises administration of one or more epigenetic modulatory compounds. As used herein, "epigenetic" is intended to refer to the physical changes that are imposed in a cell upon chromosomes and genes wherein the changes affect the functions of the DNA and genes in the chromosomes and which do not alter the nucleotide sequence of the DNA in the genes. Representative examples of epigenetic modulations include, but are not limited to, covalent chemical modifications of DNA such as methylation and acetylation as well as non-covalent and non-chemical modifications of DNA-DNA super-coiling and association with chromosomal proteins like histones. Representative, non-limiting examples of the results of epigenetic changes include increasing or decreasing the levels of RNAs, and thereby protein products, produced by certain genes and/or changing the way that transcription factors bind at to gene promoters.

Suitable epigenetic modulatory compounds for use in the methods of the present invention include, without limitation, one or more of histone deacetylase (HDAC) inhibitors, azocytidine, BET inhibitors, EZH2 inhibitors, and/or dotIL. In some embodiments, the epigenetic modulatory compounds are one or more of vorinostat (Merck), romidepsin (Celgene), decitabine (Otsuka); and 5-azocytidine (Celgene), panobinostat (Novartis), or belinostat (Spectrum).

E. Cancer Treatment

The methods of the present invention may be practiced in an adjuvant setting. "Adjuvant setting" refers to a clinical setting in which an individual has a history of a proliferative disease, particularly cancer, and generally (but not necessarily) has been responsive to therapy, which includes, but is not limited to, surgery, radiotherapy, and/or chemotherapy. However, because of a history of the proliferative disease, these individuals are considered at risk of developing that disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy.

In some aspects, any of the methods described herein include the administration of a therapeutically effective amount of an anti-cancer therapy to individuals in need thereof. As used herein, a "therapeutically effective amount" or "therapeutically effective dosage" of an anticancer therapy is an amount sufficient to effect beneficial or desired results. For therapeutic use, beneficial or desired results include clinical results such as decreasing one or more symptoms resulting from cancer, increasing the quality of life of those suffering from cancer, decreasing the dose of other medications required to treat the cancer, enhancing effect of another medication such as via targeting, delaying the progression of the disease, and/or prolonging survival. An effective dosage can be administered in one or more administrations. For purposes of this invention, an effective dosage of an anti-cancer therapy is an amount sufficient to accomplish therapeutic treatment either directly or indirectly. As is understood in the clinical context, a therapeutically effective dosage of an anti-cancer therapy may or may not be achieved in conjunction with another anti-cancer therapy.

In some aspects, any of the methods of treatment described herein can further comprise administering one or more additional anti-cancer therapies to the individual. Various classes of anti-cancer agents can be used. Non-limiting examples include: radiation therapy, alkylating agents (e.g. cisplatin, carboplatin, or oxaliplatin), antimetabolites (e.g., azathioprine or mercaptopurine), anthracyclines, plant alkaloids (including, e.g. vinca alkaloids (such as, vincristine, vinblastine, vinorelbine, or vindesine) and taxanes (such as, paclitaxel, taxol, or docetaxel)), topoisomerase inhibitors (e.g., camptothecins, irinotecan, topotecan, amsacrine, etoposide, etoposide phosphate, or teniposide), podophyllotoxin (and derivatives thereof, such as etoposide and teniposide), antibodies (e.g., monoclonal or polyclonal), tyrosine kinase inhibitors (e.g., imatinib mesylate (Gleevec® or Glivec®)), hormone treatments, soluble receptors and other antineoplastics (e.g., dactinomycin, doxorubicin, epirubicin, bleomycin, mechlorethamine, cyclophosphamide, chlorambucil, or ifosfamide).

F. T Cell Agonists

In some embodiments of any of the methods disclosed herein, the method further comprises administration of one or more compounds that activate T cells. These polypeptides, often called "stimulatory checkpoint molecules" are members of the tumor necrosis factor (TNF) receptor superfamily and the B7-CD28 superfamily. Non-limiting examples of T cell agonists appropriate for use in the present invention include, without limitation, activators of CD27 (e.g. CDX-1127 (Celldex Therapeutics)), GITR, B7-H3, CD28 (e.g. TGN1412), CD40, interleukin-2 receptor subunit beta (ILR2P; a.k.a. CD122; e.g., NKTR-214), CD137 (a.k.a. TNFRSF9, 4-1BB, and induced by lymphocyte activation (ILA)), ICOS, and/or OX40 (a.k.a. CD134 and TNFRSF4; e.g., MEDI0562, MEDI6469 and MEDI6383 (AstraZeneca)).

G. Molecular Adjuvants

In some embodiments of any of the methods disclosed herein, the method further comprises administration of one or more molecular adjuvants. As used herein, "molecular adjuvant" refers to molecules that enhance the immune response which include, without limitation, agents that activate dendritic cells. Molecular adjuvants can include, without limitation, proteins, lipids, nucleic acids, carbohydrates, or chemical compounds for which dendritic cells have a receptor whose occupancy leads to an intracellular signal transduction and a change in the dendritic cell phenotype resulting in an improvement in the quantity or quality of the ensuing immune response. Non-limiting examples of molecular adjuvants include TNF receptor superfamily (TNFRSF) agonists, Toll-like receptor (TLR) ligands, and intracellular DNA sensor agonists.

1. TNFRSF Agonists as Molecular Adjuvants

The TNFRSF includes many important receptors on dendritic cells, macrophages, and T cells. For example, cluster of differentiation 40, (CD40) is a costimulatory protein found on antigen presenting cells and is required for their activation. The binding of CD 154 (CD40L) on Tx cells to CD40 activates antigen presenting cells and induces a variety of downstream effects. CD40L strongly up-regulates the expression of CD80 and CD86 on DCs and causes CD4+ T cells to differentiate toward Th1 cells.

Other TNFRSF agonists that have been shown to have significant potential as molecular adjuvants include, without limitation, 4-IBB, CD30, herpes virus entry mediator, CD40, CD27, and glucocorticoid-induced TNFR-related protein (GITR), whose ligands are 4-1BBL, CD30L, LIGHT, CD27L/CD70, and GITRL, respectively (So et al, (2006), *Int. J. Hematol.* 83, 1-11).

2. TLR Agonists

The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-IR) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLR-1/2 agonist; CFA, a TLR-2 agonist; MALP2, a TLR-2 agonist; Pam2Cys, a TLR-2 agonist; FSL-1, a TLR-2 agonist; Hib-OMPC, a TLR-2 agonist; polyribosinic:polyribocytidic acid (Poly I:C), a TLR-3 agonist; polyadenosine-polyuridylic acid (poly AU), a TLR-3 agonist; Polyinosinic-Polycytidylic acid stabilized with poly-L-lysine and carboxymethylcellulose (Hiltonol®), a TLR-3 agonist; monophosphoryl lipid A (MPL), a TLR-4 agonist; LPS, a TLR-4 agonist; bacterial flagellin, a TLR-5 agonist; sialyl-Tn (STn), a carbohydrate associated with the MUC1 mucin on a number of human cancer cells and a TLR-4 agonist; imiquimod, a TLR-7 agonist; resiquimod, a TLR-7/8 agonist; loxoribine, a TLR-7/8 agonist; and unmethylated CpG dinucleotide (CpG-ODN), a TLR-9 agonist.

3. Intracellular DNA Sensor Agonists

The cGAS-STING pathway is a component of the innate immune system that functions to detect the presence of cytosolic DNA and, in response, trigger expression of inflammatory genes. DNA is normally found in the nucleus of the cell. Localization of DNA to the cytosol is associated with tumorigenesis or viral infection. The cGAS-STING pathway acts to detect cytosolic DNA and induce an immune response.

Upon binding DNA, the protein cyclic GMP-AMP Synthase (cGAS) triggers dimerization of AMP and GMP to form cyclic GMP-AMP (cGAMP). cGAMP binds to Stimulator of Interferon Genes (STING) which triggers TBK1 to phosphorylate downstream transcription factors IRF3, which induces the type 1 IFN response, and STATE, which induces chemokines such as CCL2 and CCL20 independently of IRF3 (Burdette et al., 2011, *Nature* 478, 515-18). The signaling pathways activated by STING combine to induce an innate immune response to cells with ectopic DNA in the cytosol. Loss of STING activity inhibits the ability of mouse embryonic fibroblasts to fight against infection by certain viruses, and more generally, is required for the type 1 IFN response to introduced cytosolic DNA (Ishikawa, et al., 2009, *Nature* 461, 788-92).

DNA has been shown to be a potent adjuvant to boost the immune response to antigens encoded by vaccines. cGAMP, through IRF3 activation of STING, stimulates transcription of interferon. This makes cGAMP a potential vaccine adjuvant capable of boosting inflammatory responses (Diner et al., 2013, *Cell Rep.*, 3(5): 1355-61). Studies have shown that vaccines encoded with the chicken antigen, ovalbumin (OVA), in conjunction with cGAMP, were able to activate antigen-specific T and B cells in a STING-dependent manner in vivo. When stimulated with OVA peptide, the T cells from mice vaccinated with OVA+cGAMP were shown to have elevated IFN-g and IL-2 when compared to animals receiving only OVA (Xiao-Dong et al., 2013, *Science,* 341 (6152): 1390-94). Furthermore, the enhanced stability of cGAMP, due to the unique 2'-5' phosphodiester bond, may make it a preferred adjuvant to DNA for in vivo applications.

H. Micro Environment Modulators

In other embodiments of any of the methods disclosed herein, the method further comprises administration of one or more microenvironment modulators. "Microenvironment modulators" refer to factors capable of generating an immunosuppressive tumor microenvironment that supports tumor growth (Ino et al., 2013, *J Cancer Sci Ther.*, S13). One such modulator is indoleamine (2,3)-dioxygenase (IDO) which was also identified as a checkpoint protein (see supra). IDO is an enzyme with two isoforms (IDO1 and IDO2) that acts at the first step in the metabolic pathway that breaks down the essential amino acid tryptophan. IDO exerts its immunomodulatory effects by shutting down the effector T cells of the immune system (Smith et al., *Cancer Discov.* 2012; 2(8):772-735). IDO expression also directly activates the regulatory T cells, a subset of T cells whose major function is to shut down T cell-mediated immunity at the end of an immune reaction.

Another microenvironment modulator is tryptophan 2,3-dioxygenase (TDO). TDO plays a central role in the physiological regulation of tryptophan flux in the human body. It catalyzes the first and rate limiting step of tryptophan degradation along the kynurenine pathway thereby regulating systemic tryptophan levels. It has been shown that tryptophan 2,3-dioxygenase is expressed in a significant proportion of human tumors (Pilotte et al., 2012, *Proceedings of the National Academy of Sciences of the United States of America* 109(7):2497-502). In the same study, tryptophan 2,3-dioxygenase expression by tumors prevented their rejection by immunized mice. A tryptophan 2,3-dioxygenase inhibitor developed by the group restored the ability of these mice to reject tryptophan 2,3-dioxygenase-expressed tumors, demonstrating that tryptophan 2,3-dioxygenase inhibitors display potential in cancer therapy.

Other microenvironment modulators suitable for use in the methods of the present invention can include, without limitation, IDO, TDO, CD73, COX2 inhibitors, CD39 inhibitors, and A2A receptor agonists.

I. Chemokine Receptor Antagonists

In yet other embodiments of any of the methods disclosed herein, the method further comprises administration of one or more chemokine receptor antagonists. Chemokine receptors are G protein-coupled receptors containing seven transmembrane domains that are found predominantly on the surface of leukocytes. Chemokine receptors are divided into different families: CXC chemokine receptors, CC chemokine receptors, CX3C chemokine receptors and XC chemokine receptors corresponding to the four distinct subfamilies of chemokines they bind.

In some embodiments, the methods of the present invention include one or more antagonists to a chemokine receptor of the CXC chemokine receptor family. Suitable CXC family member targets include CXCR1 (a.k.a. IL8RA or CD181), which is thought to have a role in the cell growth and angiogenesis required for tumor survival and CXCR4 (a.k.a. fusin or CD 184).

In other embodiments, the methods of the present invention include one or more antagonists to a chemokine receptor of the CC chemokine receptor (or beta chemokine receptor) family which can include, without limitation, CCR2, CCR5, and/or CCR4.

J. Cytokine Therapies

In other embodiments of any of the methods disclosed herein, the method further comprises administration of one or more cytokine therapies. Cytokines are a broad group of proteins produced by many types of cells present within tumors which have the ability to modulate immune responses. These immune-modulating effects allow them to be used as drugs to provoke an immune response. Two commonly used groups of cytokines are interferons and interleukins.

Non-limiting examples of cytokine therapies appropriate for use in the present invention include, without limitation, Type IIFN (IFNa), IL-2, IL-7, IL-15, IFNy, IL-10, IL-12, IL-21, FLT3, and/or anti-TGFp. The receptors for these proteins (e.g., IL-2R, IL-7R, IL-15R, IL-10R, IL-12R, or IL-21R, etc.) can also be targeted (e.g., with an activating drug (e.g. small molecule), antibody, or polypeptide).

K. Other Immunotherapies

Other immunotherapies appropriate for use with the methods disclosed herein include, without limitation, immunogenic chemotherapy, XRT, oncolytic viruses, cryotherapy, TACE, intratumoral injection of immunomodulatory agents, targeted therapies for oncogenic pathways (MAPK, beta catenin, PI3K/PTEN, FGFR3, etc.), epigenetic therapy, CSF1/CSFR1 depleting antibodies and anti-CCR4 (e.g., mogamulizumab; Kyowa), anti-IL-8/IL-8R, anti-CCR2, anti-CCR5, anti-CXCRUCXCR2, anti-CTLA4, anti-CCR4, anti-CCR8, anti-CD25, anti-KIR, anti-NKG2a, anti-NKG2DL (MICA), arginase, IDO/TDO, adenosine, A2AR, CD39, CD73, PI3K gamma, anti-NKG2D, CD94 as well as therapies for activating or inhibiting one or more of CD47/ SIRPa, Mer/Axl/Tyro3, TIM3, MFG-E8/GAS6, and/or DD1 alpha. Further information regarding immunotherapies can be found in Adams et al., 2015, *Nature Rev. Drug. Disc,* 14:603-22; Weinmann, 2016, ChemMedChem, 11:450-66; and Zhan et al., 2016, *Drug Disc. Today,* 21(6):1027-36, the disclosures of which are incorporated by reference herein.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

Example 1: Treatment of Tumors in Syngeneic Immune Competent Mice with a Combination of PTC Read-Through Compounds (RTCs) and Nonsense-Mediated Decay Inhibitors (NMDIs)

This Example demonstrates that inhibition of the nonsense mediated decay (NMD) pathway by a combination of PTC read-through promoting compounds and nonsense mediated decay inhibitor (NMDI) results in the generation of an immune response and shrinkage of tumors.

Materials and Methods

Syngeneic immune competent tumor models are created with murine cancer cell lines, examples include pancreatic (PanO2), prostate (RM1), colon (CT-26, Colon-26, MC38-26), kidney (Renca), bladder (MBT-2), lung (LL/2, KLN205), melanoma (B16BL6, B16F10, S91), breast (4T1, EMT6, JC), fibrosarcoma (WEHI-164), leukemia (C1498, L1210), liver (H22, Hepal-6), lymphoma (A20, EL-4, E.G&-OVA, L5178-R, P388D1), mastocytoma (P815), myeloma (MPC-11), neuroblastoma (Neuro-2a) among others (world wide web.crownbio.com/oncology/in-vivo-services/syngeneic-tumour-models/). Mice receive a suspension of tumor cells injected subcutaneously which develops into a tumor approximately 4-6 weeks after injection.

To test the efficacy of treatments on early established mouse tumors, cohorts of 10 mice per group receive drugs (or sham controls) beginning on days 3-7 or when tumors are palpable. Drugs are given on a daily basis, twice daily basis, several times a week or dosed continuously until mice are sacrificed at 4-6 weeks or when tumors achieve 3-5 cm in size or become ulcerated. During treatment, tumor volume is determined using three-dimensional measurements by calipers three times a week. Tumors are collected after sacrificing and are weighed to determine final tumor volume.

Other tumor-bearing cohorts are sacrificed at earlier time points to examine immune T cell responses in the tumors. Intratumoral immune response is assessed using flow cytometric enumeration, CD4 and CD8 effector T cell responses as well as $T_{reg}$ responses. Animals that are cured are re-challenged with the identical tumor to determine whether memory anti-tumor responses are induced against neoantigens.

The same tumor cell lines are treated in vitro with drugs to identify neoantigens. RNAseq is performed before and after treatment, and computationally analyzed to predict neoantigens. These same drug treated cell lines are used to stimulate T cells obtained from tumor-bearing drug treated animals to demonstrate induced neoantigen-specific T cell responses.

Where the drug is a combination of an RTC and an NMDI, a cohort of 10 mice per group are treated with 10 or 100 mg/kg of the drugs by intraperitoneal injection, oral gavage or other route of administration with the drugs (resuspended in DMSO) and injections are performed at a concentration of 30 mg/kg 2-4 times daily.

Example 2: Treatment of Tumors in Syngeneic Immune Competent Mice with a Combination of RTCs, NMDIs, and Immunotherapy Agent This Example shows the effect of treatment of tumors in syngeneic immune competent mice with a combination of RTCs and NMDIs and an immunotherapy agent. Combining these approaches (either locally or systemically) with an immunotherapy agent such as a checkpoint blockade could greatly enhance the efficacy of cancer immunotherapy due to the generation of robust tumor neoantigens in vivo. Awakening these previously hidden strong endogenous tumor antigens is likely to induce a round of renewed immune surveillance that could be further augmented by concomitant use of other approaches (checkpoint blockade, immune adjuvants) to drive immunity to these mutations inherent in each individual's tumor.

Currently, checkpoint blockade has been a major therapeutic advance with individuals with immunologically "hot" tumors with ongoing adaptive immunity that requires only removal of T cell inhibitory pathways to enable existing cytolytic T cells to complete their job of eradicating tumor. PTC-read-through has the potential to convert immunologically "cold" tumors to "hot" tumors, by driving new T cell expansion through an endogenous vaccinal effect, widening the potential number of patients who will receive benefit from checkpoint blockade Materials and Methods Mouse models of cancer used are as described above.

Assessment of tumor size, intratumoral immune response, CD4 and CD8 effector T cell responses, and $T_{reg}$ response are as described above.

Where the drug is a combination of an RTC and an NMDI, a cohort of 10 mice per group are treated with 10 or 100 mg/kg of the drugs by intraperitoneal injection, oral gavage or other route of administration with the drugs (resuspended in DMSO) and injections are performed at a concentration of 30 mg/kg 2-4 times daily (Keyali et al. 2012). Examples of NMDIs include (Martin et al, Cancer research 2014).

Combination with one or more immunotherapy agents include drugs (in particular modulators of PD-1/PD-L1 and/or CTLA4) to enhance the immune response against tumors (Curran et al., *PNAS,* 2010; Duraiswamy et al., *Cancer Res* 2013). These can include but are not limited to: checkpoint inhibitors (e.g., inhibitors of PD-1, PD-L1, CTLA4, LAG3, TIM3, TIGIT, and/or VISTA), T cell agonists (e.g., agonists of CD27, OX-40, GITR, ICOS, B7-H3, and/or CD137), molecular adjuvants: (e.g., CD40, TLR ligands, and/or intracellular DNA sensor agonists (STING), microenvironment modulators (e.g., CD73, IDO, TDO, COX2 inhibitors, CD39 inhibitors, A2A receptor agonists), chemokine receptor antagonists (e.g., antagonists of CXCR1, CCR2, CCR5, CCR4, and/or CXCR4), and/or cytokine therapies (e.g. IL-2, IL-15, IFNy, IL-10, IL-12, and/or anti-TGFp.

Example 3: Combination of RTC and NMDI with an Epigenetic Modulatory Drug

This Example shows the effect of treatment of tumors in syngeneic immune competent mice with a combination of RTCs and NMDIs and an epigenetic modulatory drug. Addition of one or more epigenetic modulatory drug has the potential of enhancing immune recognition of neoantigens.

Materials and Methods

Mouse models of cancer used are as described above.

Assessment of tumor size, intratumoral immune response, CD4 and CD8 effector T cell responses, and $T_{reg}$ response are as described above.

Treatment of tumors with epigenetic modulators can remove repression of genes involved in the immune response. Combination with RTC and NMDI with an epigenetic modulatory drug would enhance recognition of neoantigens. Non-limiting examples of epigenetic modulatory drugs include, without limitation, HDAC inhibitors, azocytidine, BET inhibitors, EZH2 inhibitors, and/or dotlL inhibitor (e.g., pinometostat).

Example 4: Combination of RTC and NMDI with Radiation Therapy

This Example shows the effect of treatment of tumors in syngeneic immune competent mice with a combination of RTCs and NMDIs and radiation therapy. Treatment with an RTC and NMDI drug prior to radiation therapy (RT) would increase the expression of neoantigens in the tumor prior to immuno stimulatory cell death, leading to enhanced neoantigen presentation.

Materials and Methods

Mouse models of cancer used are as described above.

Assessment of tumor size, intratumoral immune response, CD4 and CD8 effector T cell responses, and $T_{reg}$ response are as described above.

Continual treatment with RTC and NMDI during radiation therapy (RT) targeted to a tumor has the potential to generate neoantigens via mutagenesis and DNA damage. Release of these antigens during cell death in conjunction with proinflammatory signals that trigger the immune response to activate tumor-specific T cells. Radiation therapy can affect the tumor microenvironment and enhance infiltration of activated T-cells, and overcome barriers of tumor rejection. Combination of an RTC and NMDI drug and immunotherapy agent (Example 4) with RT would enhance effects of radiation on both priming (antigen presentation) and effector phases of the immune response in an individual patient, by enhancing expression of neoantigens. (Demaria et al, *JAMA Oncology* 2015).

Example 5: Combination of RTC and NMDI with Chemotherapy

This Example shows the effect of treatment of tumors in syngeneic immune competent mice with a combination of RTCs and NMDIs and chemotherapy. Treatment with an RTC and NMDI drug prior to chemotherapy would increase the expression of neoantigens in the tumor prior to immunostimulatory cell death, leading to enhanced neoantigen presentation.

Materials and Methods

Mouse models of cancer used are as described above.

Assessment of tumor size, intratumoral immune response, CD4 and CD8 effector T cell responses, and $T_{reg}$ response are as described above.

Continual treatment with RTC and NMDI during chemotherapy has the potential to generate neoantigens via mutagenesis and DNA damage, and release of these antigens during cell death in conjunction with proinflammatory signals that trigger the immune response to activate tumor-specific T cells. Chemotherapy can affect the tumor microenvironment and enhance infiltration of activated T-cells, and overcome barriers of tumor rejection. Combination of an RTC and NMDI drug and immunotherapy agent (Example 4) with chemotherapy would enhance effects of chemotherapy on both priming and effector phases of the immune response in an individual patient, by enhancing expression of neoantigens.

Example 6: Combination of RTC and NMDI of Oncolytic Viruses

This Example shows the effect of treatment of tumors in syngeneic immune competent mice with a combination of RTCs and NMDIs and oncolytic viruses.

Materials and Methods

Mouse models of cancer used are as described above.

Assessment of tumor size, intratumoral immune response, CD4 and CD8 effector T cell responses, and $T_{reg}$ response are as described above.

Other approaches to induce immunogenic cell death include the use of oncolytic viruses to selectively kill tumor cells. Thus, prior treatment of patients with RTC and NMDI would enable oncolytic viruses to improve antigen presentation of the induced neoantigens, and subsequently enhanced T cell responses.

Example 7: Combination of RTC and NMDI with Vaccine Therapy

This Example shows the effect of treatment of tumors in syngeneic immune competent mice with a combination of RTCs and NMDIs and vaccine therapy.

Materials and Methods

Mouse models of cancer used are as described above.

Assessment of tumor size, intratumoral immune response, CD4 and CD8 effector T cell responses, and $T_{reg}$ response are as described above.

Neoantigen vaccination is emerging as a potentially effective vaccine approach in cancer. To date, these neoantigens have included amino acid substitutions, whereas RTC and NMDI compounds will broaden the scope of neoantigens beyond single amino acid substitutions. Abnormal peptides generated from RTC and NMDI, or DNA or RNA encoding those products, represent components of personalized vaccines. Transcriptional profiling of patient tumors treated with RTC or NMDI provides candidate abnormal read-through proteins that could be used to generate such vaccines. Whole tumors treated with RTC and NMDI may also be used as the basis for whole-cell vaccines. Such vaccines against induced neoantigens can be combined with any of the agents in these Examples, in addition to other vaccines.

Example 8: Combination of RTC and NMDI with CAR-T Cells or Patient-Derived Tumor Infiltrating Lymphocytes (TILs)

This Example shows the effect of treatment of tumors in syngeneic immune competent mice with a combination of RTCs and NMDIs and CAR-T cells or patient-derived tumor infiltrating lymphocytes.

Materials and Methods

Mouse models of cancer used are as described above.

Assessment of tumor size, intratumoral immune response, CD4 and CD8 effector T cell responses, and $T_{reg}$ response are as described above.

T cells that are elicited in patients treated with RTC and NMDI will be induced that recognize the neoantigens generated by these drugs. These specific T cells could be expanded ex vivo and re-infused into patients directly, or their TCRs could be cloned and used to engineer CAR-T cells for re-infusion.

Example 9: Use of NMDI in Combination with Immunotherapy Agents and a Read-Through Inhibitor Compound (RTC) in a Mouse Tumor Model This Example evaluated the effectiveness of a combination of a RTC, immunotherapy agents, and a compound that inhibits nonsense-mediated decay for the treatment of tumor-bearing C57BL/6 mice.

Materials and Methods

Animals: Female 6-8 week old (estimated age at inoculation) C57BL/6 mice were obtained from Shanghai Lingchang Bio-Technology Co. Ltd (LC, Shanghai, China). The animals were housed at 20~26° C. with a 12 hours light and 12 hours darkness cycle.

Cell Culture: MC38 tumor cells were maintained in vitro as a monolayer culture in DMEM medium supplemented with 10% fetal bovine serum at 37° C. in an atmosphere of 5% CO2 in air. The tumor cells were routinely subcultured twice weekly. Cells in an exponential growth phase were harvested and counted for tumor inoculation.

Therapeutic compounds: Anti-PD-1 and anti-CTLA-4 antibodies were obtained from BioXCell as was an anti-CD8 antibody. The nonsense mediated decay inhibitor NMDI14 (4,5-Dimethyl-2-[[2-(1,2,3,4-tetrahydro-6,7-dimethyl-3-oxo-2-quinoxalinyl)acetyl]amino]-3-thiophenecarboxylic acid ethyl ester, Ethyl 2-{[(6,7-dimethyl-3-oxo-1,2,3,4-tetrahydro-2-quinoxalinyl)acetyl]amino}-4,5-dimethyl-3-thiophenecarboxylate) was obtained from ChemBridge Corp. (La Jolla, CA). The RTC Ataluren (PTC124) was obtained from Selleck Chemicals (Houston, TX). Compounds were formulated as shown in Table 1.

TABLE 1

Therapeutic compound formulations.

| Compounds | Package | Preparation | Concentration (mg/ml) | Storage |
|---|---|---|---|---|
| Vehicle 1 20% Cremophor-EL + 75% saline | — | 4 ml Cremophor-EL added with 15 ml saline. Vortex and sonicates to make 19 ml vehicle 1 for each use. | 0 | 4° C. |

TABLE 1-continued

Therapeutic compound formulations.

| Compounds | Package | Preparation | Concentration (mg/ml) | Storage |
|---|---|---|---|---|
| Vehicle2 20% Cremophor-EL + 75% saline | — | 10 g HP-13-CD be measured, 50 ml PBS added. Vortex and sonicated to make Vehicle 2. | 0 | 4° C. |
| NMDI14 | 200 mg/vial | 10 mg Compound C will be measured, 1 ml DMSO will be added. Vortex and sonicate to make stock solution 1. | Stock solution 1 | 4° C. |
| | | Vehicle: 5% DMSO + 20% Cremophor-EL + 75% saline Mix 1 ml stock solution 1 with 19 ml vehicle 1 to make 20 ml dosing solution. | 0.5 | 4° C. |
| PTC124 | 800 mg/vial | 40 mg PTC124 measured, 0.4 ml DMSO will be added. Vortex and sonicate to make stock solution 2. | Stock solution 2 | 4° C. |
| | | Vehicle: 2% DMSO + 98%(20% HP-P-CD PBS buffer) Dilute 0.4 ml stock solution2 with 19.6 ml 20% HP-J3-CD PBS buffer. Vortex and sonicate to make 20 ml dosing solution for each use. | 2 | 4° C. |
| Anti-PD-1 | 8.12 mg/ml | Dilute 1.478 ml 8.12 mg/ml Anti-PD1 antibody solution with 10.523 ml PBS make 12.001 ml dosing solution for each use. | 1 | Immediate use |
| Anti-CTLA-4 | 7.62 mg/ml | Dilute 1.575 ml 7.62 mg/ml CTLA-4 antibody solution with 10.426 ml PBS make 12.001 ml dosing solution for each use. | 1 | Immediate use |
| Anti-CD8 | | Dilute 0.698 ml 5.73 mg/ml anti-CD8 antibody solution with 3.302 ml PBS make 4 ml dosing solution for each use. | 1 | Immediate use |

Tumor Inoculation: Each mouse was inoculated subcutaneously at the right lower flank region with MC38 tumor cells ($1\times10^6$) in 0.1 mL of PBS for tumor development. The treatments were started when the mean tumor size reaches approximately 50 mm$^3$. Compounds were administered and the animal numbers in each study group are shown in Table 2. The date of tumor cell inoculation was denoted as day 0.

Group assignment: Before grouping and treatment, all animals were weighed and the tumor volumes measured using a caliper. Tumor volume was used as numeric parameter to randomize selected animals into specified groups in order to minimize systematic error. The grouping was performed by using StudyDirector™ software (Studylog Systems, Inc. CA, USA). One optimal randomization design (generated by Matched distribution) showing minimal group to group variation in tumor volume was selected for group allocation.

TABLE 2

Administration of the test articles and the animal numbers in each study group

| Group | N | Treatment | Dose (mg/kg) | Dosing Route | Schedule |
|---|---|---|---|---|---|
| 1 | 8 | Vehicle(PBS) | | i.p. | QD × 3 weeks |
| 2 | 8 | PTC124 NMDI14 | 20 5 | i.p. | QD × 3 weeks |
| 3 | 8 | Anti-PD-1 | 10 | i.p. | BIW × 3 weeks |
| 4 | 8 | Anti-CTLA-4 | 10 | i.p. | BIW × 3 weeks |
| 5 | 8 | Anti-PD-1 Anti-CTLA-4 | 10 10 | i.p. | BIW × 3 weeks |
| 6 | 8 | NMDI14 PTC124 Anti-PD-1 | 5 20 10 | | QD × 3 weeks BIW × 3 weeks |
| 7 | 8 | NMDI14 PTC124 Anti-CTLA-4 | 5 20 10 | | QD × 3 weeks BIW × 3 weeks |
| 8 | 8 | NMDI14 PTC124 Anti-PD-1 Anti-CTLA-4 | 5 20 10 10 | i.p | QD × 3 weeks BIW × 3 weeks |

Note:
N: animal number;
Dosing volume was 10 μl/g;
PTC124 and NMDI14 were given the first dose at randomization (tumor size ~50 mm$^3$).
CTLA-4 and PD-1 antibody were given routinely when tumor size reached (75-100 mm$^3$), which was 3-4 days after giving PTC124 and NMDI14.
If test compounds and antibodies were administrated on the same day, PTC124 and NMDI14 were given in the morning and antibodies given in the afternoon.

FACS analysis: Tumor cells were isolated from each treatment group and FACS analysis performed according to methods which are well known in the art. Reagents used for FACS analysis are shown in Table 3 below.

TABLE 3

Reagents used for FACS analysis of tumor cells.

| Marker | Cat. | | Vender | Isotype |
|---|---|---|---|---|
| CD45 | AF488 | 103122 | Biolegend | Rat IgG2b, k |
| CD3 | APC-CY7 | 100222 | Biolegend | Armenian Hamster IgG1, k |
| CD4 | BV510 | 100449 | Biolegend | Rat IgG2b, k |
| CD8 | PE | 100708 | Biolegend | Rat IgG2a, k |
| L/D dye | BUV395 | L34962 | Invitrogen | — |

Immunohistochemistry (IHC): Formalin-fixed paraffin-embedded (FFPE) tissue from tumor samples were sectioned to 4 µm. Antigen retrieval (AR) was conducted at 100° C., in EDTA buffer, at pH 9.0 for 20 min. Primary antibody (diluted with validated concentration), RT 60 min+ secondary antibody (ready-to-use), RT 60 min+Bond Polymer Refine Detection. Antibodies and reagents used are shown in Table 4.

TABLE 4

Antibodies and reagents used in IHC experiments.

Primary Ab

| Antibodies | Company | Cat# | Type | Reactivity | Application | Concentration | Dilution |
|---|---|---|---|---|---|---|---|
| CD3 | Abcam | Ab5690 | Rb pAb | Hu, Ms, Rat | IHC-P | 0.2 mg/ml | 1:100 |
| CD8 | Abbiotec | 250596 | Rb pAb | Ms, Rat | IHC-P | 1 mg/ml | 1:400 |

Secondary Ab

| Antibodies | Company | Cat# | Detail information |
|---|---|---|---|
| Goat anti-Rb IgG | Leica | DS9800 | Anti-rabbit Poly-HRP-IgG (<25 µg/mL) containing 10% (v/v) animal serum in tris-buffered saline/0.09% ProClin™ 950 (ready-to-use) |

Results:

After tumor cell inoculation, the animals were checked daily for morbidity and mortality as well as any effects of tumor growth and treatments on normal behavior such as mobility, visual estimation of food and water consumption, body weight gain/loss, eye/hair matting and any other abnormal effect. Tumor volumes were measured twice weekly at least in two dimensions using a caliper, and the volume expressed in $mm^3$ using the formula: $V=0.5\ a \times b^2$ where a and b are the long and short diameters of the tumor, respectively.

Mean tumor volume for each treatment group over the course of the study is shown in Table 5 while the percent inhibition of tumor volume is shown in Table 6.

TABLE 5

Mean tumor volume (mm) (+/− standard error of the mean)

| Group | Day 9 | Day 12 | Day 15 | Day 18 | Day 22 | Day 25 | Day 29 | Day 32 |
|---|---|---|---|---|---|---|---|---|
| 1 | 51.97 | 84.06 | 130.14 | 288.61 | 478.07 | 800.52 | 1258.55 | 1783.31 |
|   | (2.78) | (7.26) | (14.38) | (42.26) | (59.47) | (85.67) | (109.08) | (166.07) |
| 2 | 51.60 | 75.75 | 126.43 | 229.57 | 396.58 | 740.21 | 1203.80 | 1847.51 |
|   | (3.07) | (4.35) | (11.05) | (16.98) | (46.29) | (108.23) | (198.90) | (282.24) |
| 3 | 52.13 | 77.41 | 156.84 | 235.08 | 356.65 | 580.19 | 819.16 | 1186.59 |
|   | (2.66) | (5.02) | (17.03) | (18.74) | (34.77) | (73.20) | (92.78) | (167.50) |
| 4 | 51.98 | 69.50 | 148.03 | 201.18 | 338.87 | 502.47 | 737.46 | 997.16 |
|   | (2.61) | (3.13) | (4.64) | (14.54) | (39.46) | (66.04) | (103.25) | (125.74) |
| 5 | 51.99 | 86.86 | 162.86 | 226.06 | 290.45 | 421.74 | 543.10 | 811.76 |
|   | (2.75) | (7.40) | (13.78) | (24.42) | (34.86) | (69.42) | (94.42) | (133.83) |
| 6 | 52.09 | 67.76 | 130.84 | 208.29 | 310.79 | 469.30 | 653.87 | 891.94 |
|   | (2.94) | (3.77) | (10.70) | (16.82) | (27.96) | (40.94) | (56.30) | (78.27) |
| 7 | 52.03 | 82.86 | 129.45 | 231.22 | 369.67 | 610.15 | 808.24 | 1252.84 |
|   | (2.97) | (9.35) | (12.49) | (32.98) | (74.51) | (121.97) | (118.22) | (165.92) |
| 8 | 51.98 | 76.73 | 131.12 | 196.83 | 234.60 | 284.96 | 350.14 | 471.39 |
|   | (2.74) | (3.41) | (14.18) | (25.85) | (41.66) | (57.91) | (79.07) | (101.05) |

TABLE 6

Percent inhibition of tumor volume for each treatment group
(negative values indicate an increase in tumor volume).

| Group | Day 9 | Day 12 | Day 15 | Day 18 | Day 22 | Day 25 | Day 29 | Day 32 |
|---|---|---|---|---|---|---|---|---|
| 2 | 0.70% | 9.88% | 2.85% | 20.46% | 17.05% | 7.53% | 4.35% | −3.60% |
| 3 | −0.31% | 7.90% | −20.52% | 18.55% | 25.40% | 27.52% | 34.91% | 33.46% |
| 4 | −0.03% | 17.31% | −13.74% | 30.29% | 29.12% | 37.23% | 41.40% | 44.08% |
| 5 | −0.04% | −3.34% | −25.14% | 21.67% | 39.25% | 47.32% | 56.85% | 54.48% |
| 6 | −0.23% | 19.38% | −0.54% | 27.83% | 34.99% | 41.38% | 48.05% | 49.98% |
| 7 | −0.12% | 1.43% | 0.53% | 19.88% | 22.67% | 23.78% | 35.78% | 29.75% |
| 8 | −0.02% | 8.71% | −0.75% | 31.80% | 50.93% | 64.40% | 72.18% | 73.57% |

Figure 2:
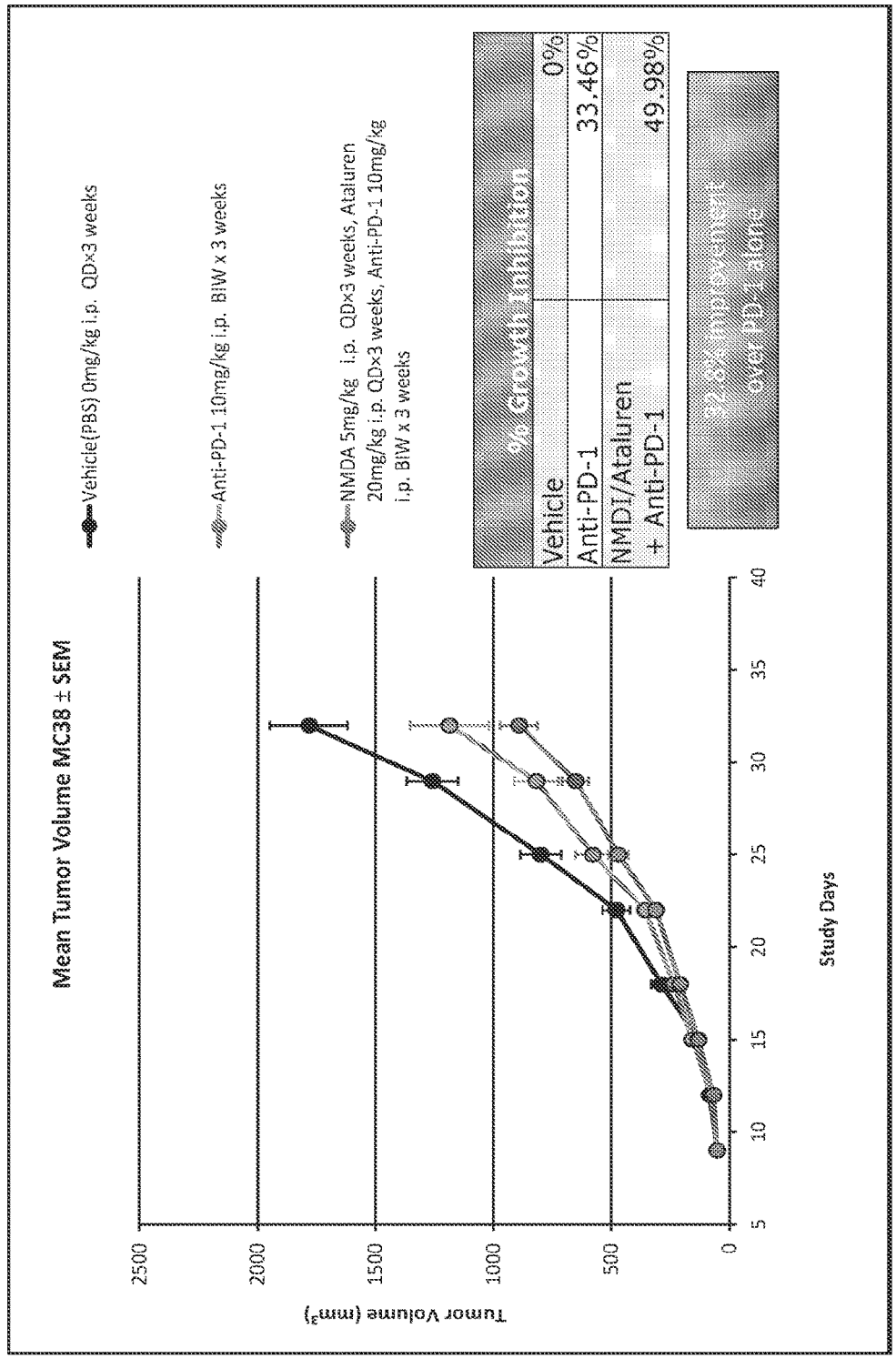
FIG. 2 depicts a graph comparing the effect of PTC124 (Ataluren) and NMDI14 and/or anti-PD-1 administration on tumor volume ($mm^3$).

As shown in Table 6, the combination of PTC124 and a nonsense mediated decay inhibitor with anti-PD-1 and anti-CTLA-4 immunotherapy resulted in an almost 75% inhibition in tumor volume (see also FIG. 1), which is greater than the result achieved by either immunotherapy alone or their combination (FIG. 2).

Figure 3:
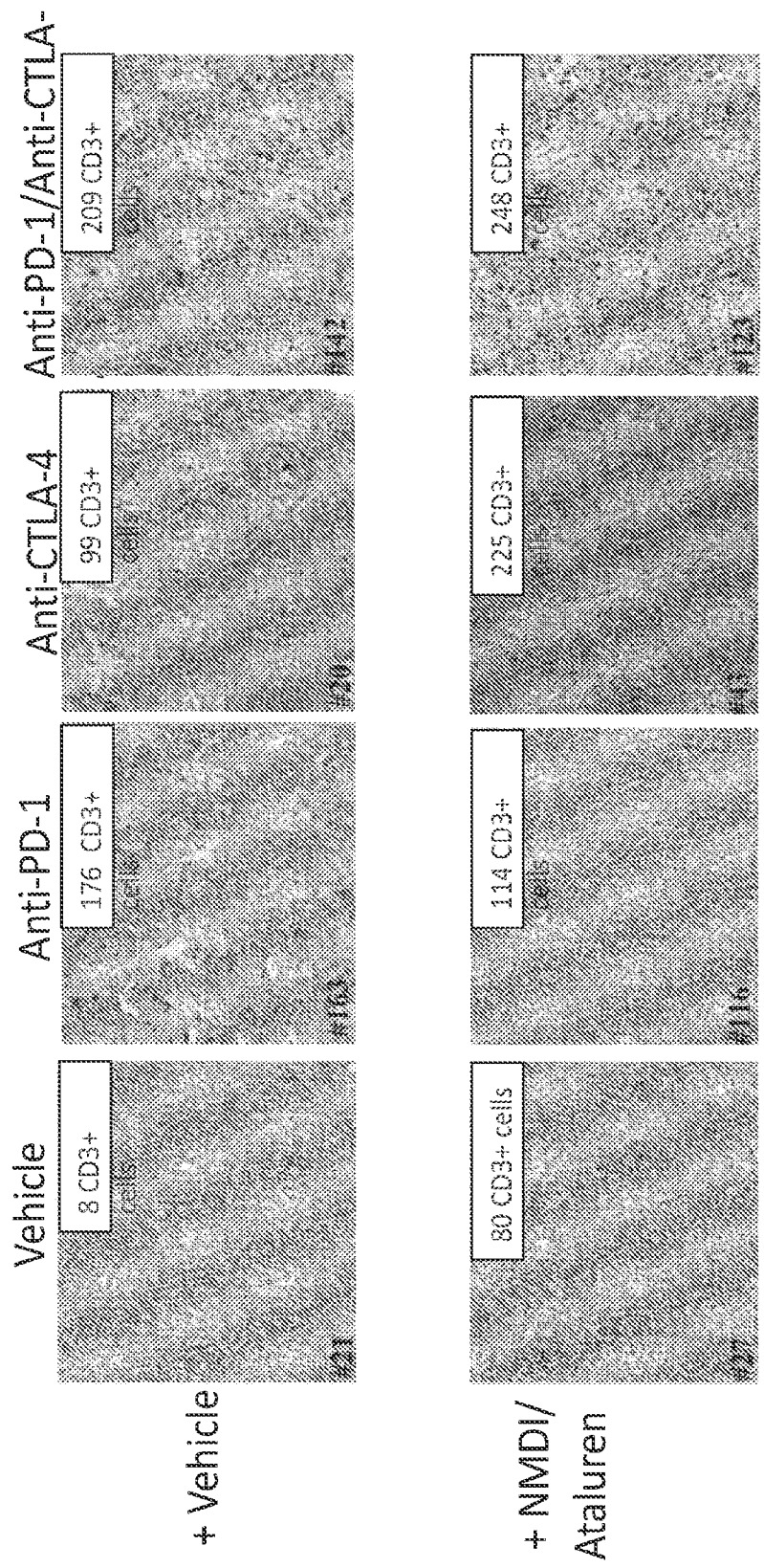
FIG. 3 depicts an image of a micrograph of sectioned tumor tissue showing immune cell infiltration following treatment.

As shown in FIG. 3, immunohistochemical analysis demonstrated that treatment with a PTC read-through inhibitor in combination with a compound that inhibits NMD resulted in significant numbers of CD3+ immune cells infiltrating tumor tissue. FIG. 3 also indicates that this effect was enhanced when treatment was combined with antibodies to PD-1 and to CTLA-4.

We claim:

1. A method of treating cancer in an individual in need thereof comprising administering to the individual an effective amount of a composition comprising ataluren and a compound that inhibits one or more immune checkpoint molecules selected from CTLA4, PD-1, PD-L1, A2AR, B7-H3, B7-H4, and TIM3.

2. The method of claim 1, wherein the cancer is selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic arcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, meduloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma, leukemias, polycythemia vera, lymphoma, multiple myeloma, Waldenstrom's macroglobulinemia, and heavy chain disease.

3. The method of claim 2, wherein the cancer is melanoma.

4. The method of claim 1, wherein the administration of the composition generates an immune response against a cancer cell.

5. The method of claim 1, wherein the compound that inhibits one or more immune checkpoint molecules is an antagonistic antibody.

6. The method of claim 5, wherein the antagonistic antibody is ipilimumab, nivolumab, pembrolizumab, durvalumab, atezolizumab, tremelimumab, or avelumab.

7. The method of claim 6, wherein the method further comprises administration of one or more epigenetic modulatory compounds.

8. The method of claim 7, wherein the epigenetic modulatory compound is one or more of vorinostat, romidepsin, decitabine, 5-azacytidine, panobinostat, and/or belinostat.

9. The method of claim 1, further comprising administering an anti-cancer agent selected from the group consisting of cisplatin, carboplatin, oxaliplatin, azathioprine, mercaptopurine, anthracyclines, vincristine, vinblastine, vinorelbine, vindesine, taxanes, camptothecins, irinotecan, topotecan, amsacrine, etoposide, etoposide phosphate, teniposide, podophyllotoxin, tyrosine kinase inhibitors, dactinomycin, doxorubicin, epirubicin, bleomycin, mechlorethamine, cyclophosphamide, chlorambucil, ifosfamide, and combinations thereof.

10. The method of claim 1, wherein the administration is oral, intravenous, sub-lingual, buccal, parenteral, rectal, vaginal, topical, or intranasal.

11. A method of generating an immune response against a neoantigen expressed on a cancer cell surface in an individual in need thereof comprising administering to the individual an effective amount of a composition comprising ataluren and a compound that inhibits one or more immune checkpoint molecules selected from CTLA4, PD-1, PD-L1, A2AR, B7-H3, B7-H4, and TIM3.

12. The method of claim 11, wherein the cancer is selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic arcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, meduloblastoma, merkel cell carcinoma, craniopharyngioma, ependymoma, pinealoma, hemangioblastoma, acoustic neuroma, oligodendroglioma, meningioma, melanoma, neuroblastoma, retinoblastoma, leukemias, polycythemia vera, lymphoma, multiple myeloma, Waldenstrom's macroglobulinemia, and heavy chain disease.

13. The method of claim 12, wherein the cancer is melanoma.

14. The method of claim 11, wherein the administration of the composition generates an immune response against a cancer cell.

15. The method of claim 11, wherein the compound that inhibits one or more immune checkpoint molecules is an antagonistic antibody.

16. The method of claim 15, wherein the antagonistic antibody is ipilimumab, nivolumab, pembrolizumab, durvalumab, atezolizumab, tremelimumab, or avelumab.

17. The method of claim 16, wherein the method further comprises administration of one or more epigenetic modulatory compounds.

18. The method of claim 17, wherein the epigenetic modulatory compound is one or more of vorinostat, romidepsin, decitabine, 5-azacytidine, panobinostat, and/or belinostat.

19. The method of claim 11, further comprising administering an anti-cancer agent selected from the group consisting of cisplatin, carboplatin, oxaliplatin, azathioprine, mercaptopurine, anthracyclines, vincristine, vinblastine, vinorelbine, vindesine, taxanes, camptothecins, irinotecan, topotecan, amsacrine, etoposide, etoposide phosphate, teniposide, podophyllotoxin, tyrosine kinase inhibitors, dactinomycin, doxorubicin, epirubicin, bleomycin, mechlorethamine, cyclophosphamide, chlorambucil, ifosfamide, and combinations thereof.

20. The method of claim 11, wherein the administration is oral, intravenous, sub-lingual, buccal, parenteral, rectal, vaginal, topical, or intranasal.

* * * * *